(12) United States Patent
Lee et al.

(10) Patent No.: US 11,452,661 B2
(45) Date of Patent: Sep. 27, 2022

(54) METHOD AND DEVICE FOR ASSISTING WALKING

(71) Applicant: Samsung Electronics Co., Ltd., Suwon-si (KR)

(72) Inventors: Jusuk Lee, Suwon-si (KR); Hyun Do Choi, Yongin-si (KR); Seungyong Hyung, Yongin-si (KR); Youngjin Park, Seoul (KR); Bokman Lim, Yongin-si (KR); Jun-Won Jang, Seoul (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 421 days.

(21) Appl. No.: 16/659,036

(22) Filed: Oct. 21, 2019

(65) Prior Publication Data
US 2020/0188214 A1 Jun. 18, 2020

(30) Foreign Application Priority Data
Dec. 13, 2018 (KR) .................. 10-2018-0160946

(51) Int. Cl.
*A61H 3/00* (2006.01)
*A61F 5/01* (2006.01)
*A61B 5/11* (2006.01)

(52) U.S. Cl.
CPC ............. *A61H 3/00* (2013.01); *A61F 5/0127* (2013.01); *A61B 5/112* (2013.01);
(Continued)

(58) Field of Classification Search
CPC .. A61H 3/00; A61H 2201/5092; A61B 5/112; A61B 5/1127; A61B 5/1128;
(Continued)

(56) References Cited

U.S. PATENT DOCUMENTS 8,500,668 B2 8/2013 Siegler et al.
9,211,201 B2 12/2015 Herr et al.
(Continued)

FOREIGN PATENT DOCUMENTS

JP 2006314670 A 11/2006
JP 2010099418 A 5/2010
(Continued)

OTHER PUBLICATIONS

J. Taborri et al., 'Gait Partitioning Methods: A Systematic Review'. *Sensors*, vol. 16, No. 66, Jan. 2016.

*Primary Examiner* — Samchuan C Yao
*Assistant Examiner* — Tyler A Raubenstraw
(74) *Attorney, Agent, or Firm* — Harness, Dickey & Pierce, P.L.C.

(57) ABSTRACT

A walking assistance device and method for providing an assist torque to an ankle of a user is provided. To provide an assist torque to an ankle of a user, the walking assistance device generates a leg image by capturing a second leg using a camera attached to a first leg, determines a gait state of the second leg based on the leg image, determines an assist torque value output to the first leg based on the gait state of the second leg, and controls a driving device such that the assist torque value is output to the first leg.

16 Claims, 24 Drawing Sheets

(52) U.S. Cl.
CPC ............ *A61H 2201/1642* (2013.01); *A61H 2201/5007* (2013.01); *A61H 2201/5064* (2013.01); *A61H 2201/5069* (2013.01); *A61H 2201/5071* (2013.01); *A61H 2201/5082* (2013.01); *A61H 2201/5084* (2013.01); *A61H 2201/5092* (2013.01); *A61H 2205/106* (2013.01)

(58) Field of Classification Search
CPC ... A61B 5/11; A61B 5/1121–3; A61B 5/1122; A61B 5/1123; A61F 5/0127
See application file for complete search history.

(56) References Cited

U.S. PATENT DOCUMENTS

| | | | |
|---|---|---|---|
| 9,642,572 B2* | 5/2017 | Mahfouz | A61B 5/1038 |
| 9,668,888 B2 | 6/2017 | Herr et al. | |
| 10,576,619 B2* | 3/2020 | Shim | B25J 9/1671 |
| 10,639,170 B2* | 5/2020 | Seo | B25J 9/0006 |
| 10,716,494 B2* | 7/2020 | Kim | A61B 5/486 |
| 2010/0324699 A1* | 12/2010 | Herr | A61F 2/66 623/27 |
| 2013/0258044 A1* | 10/2013 | Betts-Lacroix | H04N 13/243 348/E5.09 |
| 2017/0027803 A1* | 2/2017 | Agrawal | A61B 5/1122 |
| 2017/0202724 A1* | 7/2017 | De Rossi | A61H 3/00 |
| 2018/0146890 A1* | 5/2018 | Kim | A61B 5/1121 |
| 2018/0235831 A1* | 8/2018 | Jang | B62D 57/032 |
| 2019/0314185 A1* | 10/2019 | Yuge | G06K 9/00543 |
| 2019/0343707 A1* | 11/2019 | Riener | A61H 3/00 |
| 2020/0146397 A1* | 5/2020 | Coupe | B29D 35/122 |

FOREIGN PATENT DOCUMENTS

| | | | |
|---|---|---|---|
| JP | 4611580 B2 | | 1/2011 |
| JP | 5177070 B2 | * | 4/2013 |
| JP | 6161001 B2 | | 7/2017 |
| KR | 101583871 B1 | | 1/2016 |

* cited by examiner

METHOD AND DEVICE FOR ASSISTING WALKING

CROSS-REFERENCE TO RELATED APPLICATION

This application claims priority under 35 U.S.C. § 119 to Korean Patent Application No. 10-2018-0160946, filed on Dec. 13, 2018, in the Korean Intellectual Property Office, the entire contents of which are incorporated herein by reference in their entirety.

BACKGROUND

1. Field

At least one example embodiment relates to a method and/or apparatus for assisting walking of a user. For example, at least some example embodiments relate to a method and/or apparatus for providing an assist torque for assisting a gait while a user is walking.

2. Description of the Related Art

With the onset of aging societies, a growing number of people experience inconvenience and pain in walking due to reduced muscular strength or malfunctioning joint issues. Thus, interest in a walking assistance device that enables an elderly user or a patient with reduced muscular strength or joint problems to walk with less effort is growing. Also, walking assistance devices for enhancing muscular strength of a human body, for example, for military purposes are being developed.

SUMMARY

Some example embodiments relate to a method of controlling a driving device of a walking assistance device.

In some example embodiments, the method may include capturing, via a camera attached to a first leg of a user, a leg image of a second leg of the user; determining a gait state of the second leg based on the leg image; determining an assist torque value output to the first leg based on the gait state of the second leg; and controlling the driving device to output the assist torque value to the first leg.

In some example embodiments, the camera is a multi-view camera, and the capturing of the leg image includes capturing, via the multi-view camera, a plurality of leg images; and generating the leg image by merging the plurality of leg images.

In some example embodiments, the camera is an infrared camera or a thermal imaging camera.

In some example embodiments, the method further includes adjusting an orientation of the leg image to generate an adjusted leg image based on at least one of acceleration information and orientation information acquired from an inertial measurement unit (IMU) attached to at least one of the first leg and the second leg, wherein the determining of the gait state of the second leg includes determining the gait state of the second leg based on the adjusted leg image.

In some example embodiments, the determining of the gait state of the second leg includes detecting, in the leg image, a ground and the second leg; and determining the gait state of the second leg based on the ground and the second leg in the leg image.

In some example embodiments, the determining of the gait state of the second leg based on the ground and the second leg in the leg image includes determining the gait state of the second leg based on an angle between the ground and the second leg in the leg image.

In some example embodiment, the determining of the gait state of the second leg based on the ground and the second leg in the leg image includes determining a position of the second leg in the leg image; and determining the gait state based on the position of the second leg in the leg image.

In some example embodiments, the determining of the gait state based on the position of the second leg in the leg image includes determining a relative position of the second leg with respect to at least two feature positions; determining a degree of process of a gait cycle based on the relative position; and determining the gait state based on the degree of process of the gait cycle.

In some example embodiments, the determining of the gait state based on the position of the second leg in the leg image includes determining whether the second leg has passed a threshold position in a set direction based on the position of the second leg in the leg image; and determining the gait state to be a target gait state in response to the second leg passing the threshold position in the set direction.

In some example embodiments, the determining of the assist torque value output to the first leg includes determining the assist torque value for push-off of the first leg in response to the gait state of the second leg being the target gait state.

In some example embodiments, the determining of the assist torque value output to the first leg includes determining the assist torque value for dorsiflexion of the first leg in response to the gait state of the second leg being the target gait state.

In some example embodiments, the determining of the assist torque value output to the first leg includes determining the assist torque value from a set assist torque pattern based on the gait state of the second leg.

In some example embodiments, the determining of the assist torque value output to the first leg includes determining a gait state of the first leg based on the gait state of the second leg; and determining the assist torque value output to the first leg based on the gait state of the first leg.

In some example embodiments, the determining of the gait state of the first leg includes acquiring a pressure value from at least one pressure sensor attached to the first leg; and determining the gait state of the first leg based on the pressure value and the gait state of the second leg.

Some example embodiments relate to non-transitory computer-readable medium comprising computer readable instructions that, when executed, configure a computer to perform a method of controlling a driving device of a walking assistance device.

Other example embodiments relate to a walking assistance device for providing an assist torque to an ankle of a first leg of a user.

In some example embodiments, the walking assistance device may include a memory including a program for providing the assist torque; and a processor configured to execute the program to, capture, via a camera attached to the first leg of the user, a leg image of a second leg of the user, determine a gait state of the second leg based on the leg image, determine an assist torque value output to the first leg based on the gait state of the second leg, and control a driving device to output the assist torque value to the first leg such that the driving device provides the assist torque to the ankle of the first leg of the user.

Other example embodiments relate to a walking assistance device for assisting walking of a user.

In some example embodiments, the walking assistance device may include a camera configured to attach to a first leg of the user such that the camera is configured to capture a leg image of a second leg of the user; a processor configured to, determine a gait state of the second leg based on the leg image, and determine an assist torque value to output to the first leg based on the gait state of the second leg; and a driving device configured to generate an assist torque having the assist torque value.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
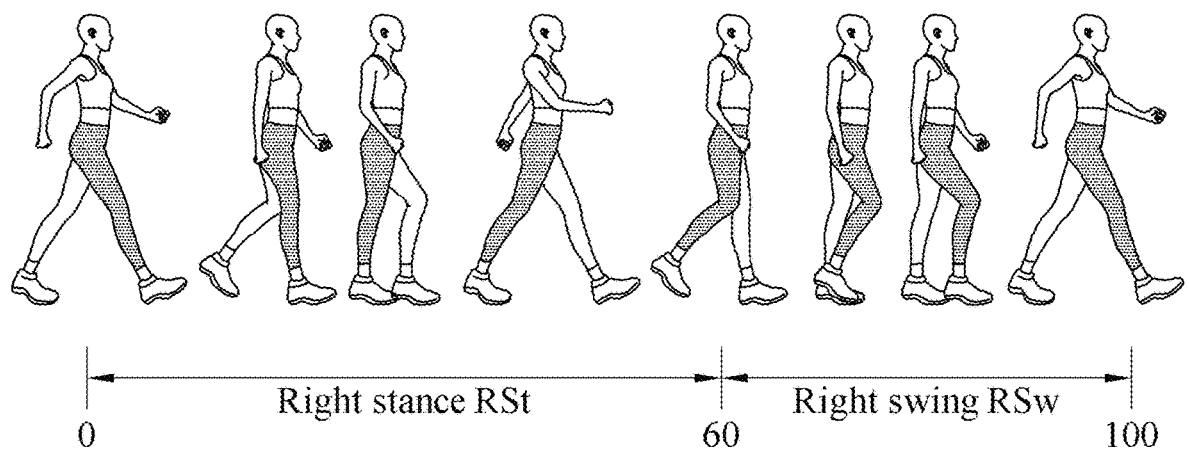
FIG. 1 illustrates a gait state according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

FIG. 1 illustrates a gait state according to at least one example embodiment.

Referring to FIG. 1, gait phases of one leg of a user for a gait may be defined (or, alternatively, predefined). For example, the gait phases may include a stance and a swing. Gait phases of a left leg may be classified into a left stance LSt and a left swing LSw. Gait phases of a right leg may be classified into a right stance RSt and a right swing RSw.

A gait cycle associated with gait phases may be mapped to a finite state machine (FSM). For example, a gait cycle of 0% may be mapped at a point in time at which the stance starts, the gait cycle of 60% may be mapped at a point in time at which the swing starts, and the gait cycle of 100% may be mapped at a point in time just before the stance starts.

The stance and the swing may be further sub-divided into a plurality of phases. For example, the stance may be sub-divided into an initial contact, a weight bearing, a middle stance, a terminal stance, and a pre-swing. The swing may be sub-divided into an initial swing, a middle swing, and a terminal swing. The example embodiment is provided as an example only, and the stance and the swing may be differently sub-divided.

Figure 2:
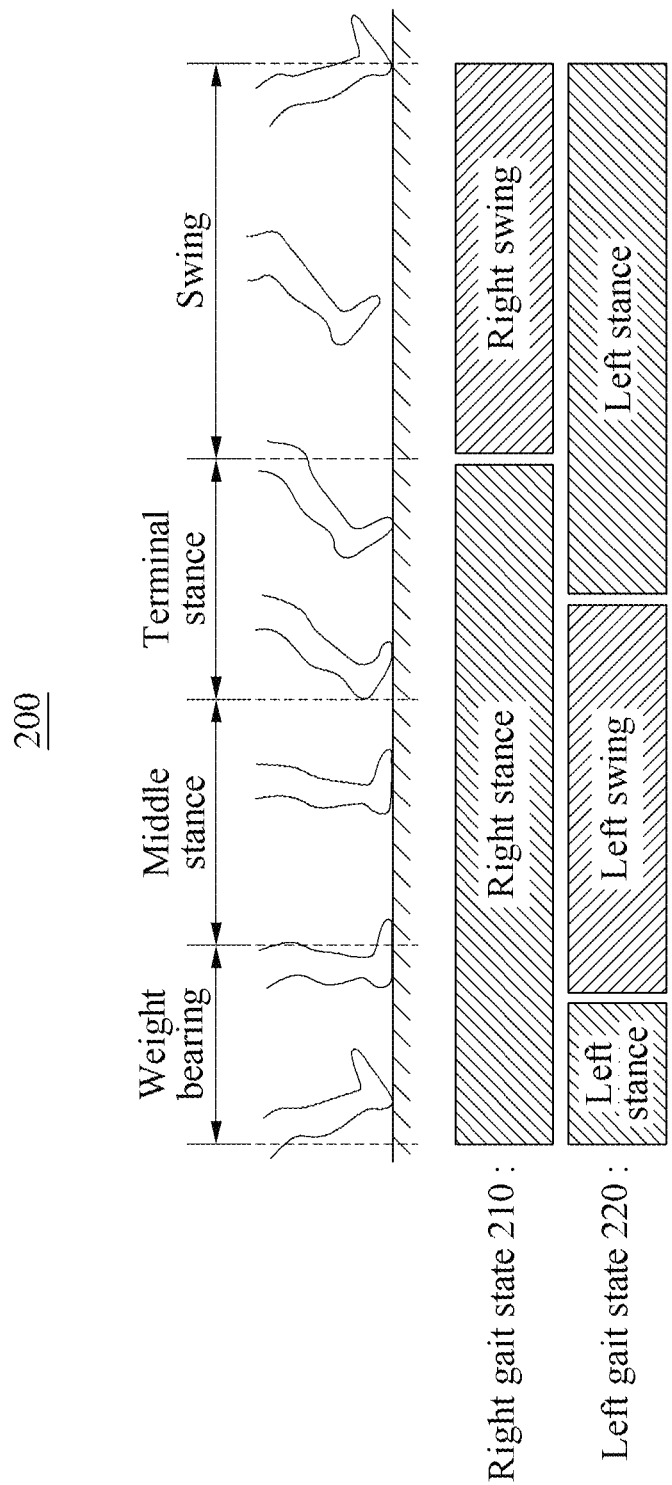
FIG. 2 illustrates a transition between gait phases according to at least one example embodiment.

FIG. 2 illustrates a transition between gait phases according to at least one example embodiment.

Referring to FIG. 2, according to a general gait mechanism, gait phases of each leg include a stance and a swing, and the stance and the swing are alternately performed for walking.

A right gait state 210 associated with a change 200 of a right leg includes a right stance and a right swing. The stance may include a weight bearing, a middle stance, and a terminal stance but is not limited thereto. A left gait state 220 associated with a change of a left leg (not shown) relative to the change 200 of the right leg includes a left stance and a left swing.

If muscular strength of an ankle of a user is reduced due to aging or diseases of the user, the user may experience discomfort with walking. An end of a foot of the user needs to be lifted to swing a leg. Otherwise, the leg to swing may hit a floor. For example, when a foot drop occurs, there is a risk of falling. To inhibit (or, alternatively, prevent) this, an angle of an ankle needs to be adjusted in response to the progress of a gait phase or a change of the gait phase. A walking assistance device may be provided to a user having difficulty in adjusting an angle of an ankle by himself or herself due to the reduced muscular strength of the ankle. The walking assistance device may be worn around the ankle of the user, determine a gait phase of the user, and output an assist torque corresponding to the determined gait phase. The ankle angle of the user may be adjusted based on the assist torque.

Figure 3:
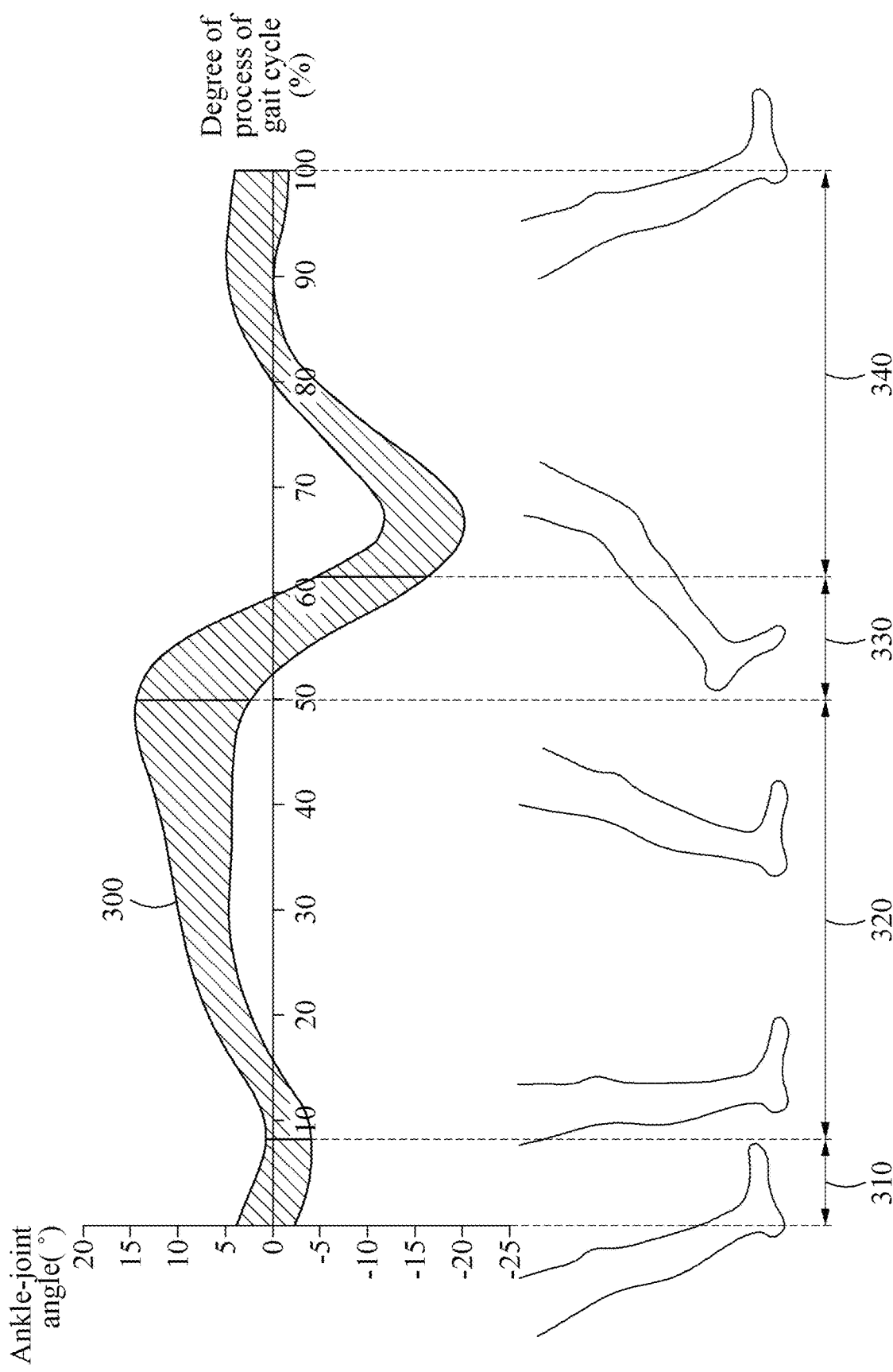
FIG. 3 illustrates a trajectory of an ankle-joint angle for a gait cycle according to at least one example embodiment.

FIG. 3 illustrates a trajectory of an ankle-joint angle for a gait cycle according to at least one example embodiment.

Referring to FIG. 3, when a user walks according to a general gait mechanism, an ankle-joint angle trajectory 300 of the user may appear as shown in FIG. 3. In the same walking state, the ankle-joint angle may vary based on a stride and a walking speed, but an ankle-joint angle trajectory for one gait cycle may show a similar pattern. The ankle-joint angle trajectory 300 is shown to have an example range of variation in a degree of progress of a desired (or alternatively, a predetermined) gait cycle.

In a case of a patient with an impaired leg, the ankle-joint angle trajectory 300 may not appear for the impaired leg. A gait mechanism for the patient may be improved by adjusting an ankle-joint angle such that an ankle joint of the impaired leg of the patient has the ankle-joint angle trajectory 300.

Figure 4:
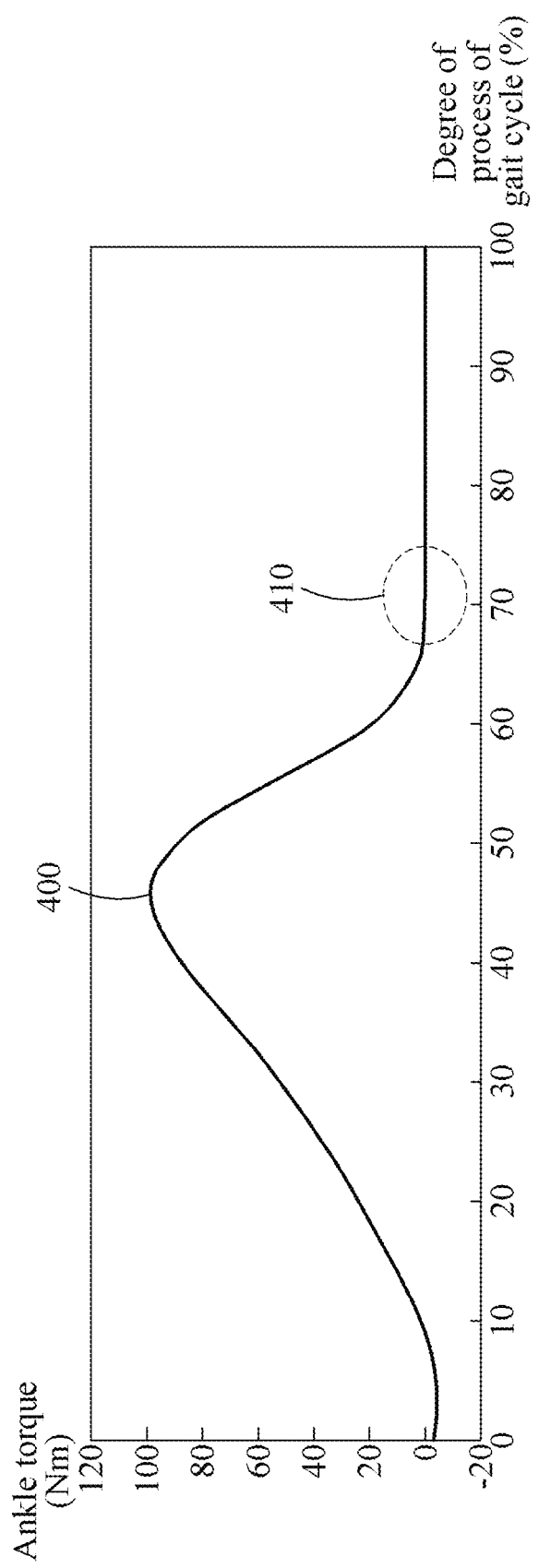
FIG. 4 illustrates a trajectory of an ankle torque for a gait cycle according to at least one example embodiment.

FIG. 4 illustrates a trajectory of an ankle torque for a gait cycle according to at least one example embodiment.

Referring to FIG. 4, when a user walks according to a general gait mechanism, an ankle torque trajectory 400 of an ankle torque output by an ankle joint of the user may appear as shown in FIG. 4. A positive ankle torque value may increase an ankle joint ankle (for example, plantar flexion) and a negative ankle torque value may reduce the ankle joint ankle (for example, dorsiflexion).

According to an aspect, a first portion 410 corresponding to an interval after an occurrence of push-off in the ankle torque trajectory 400 may be an assist torque value for dorsiflexion for inhibiting (or, alternatively, preventing) a foot drop. The assist torque value for the dorsiflexion may be a negative value.

A patient with an impaired leg may not generate an assist torque by himself or herself. Thus, to receive the assist torque, the patient may wear a walking assistance device on the impaired leg. The walking assistance device may adjust an ankle angle by outputting the assist torque through a driving device. If the assist torque for adjusting the ankle angle is not output at a proper timing, the user may feel uncomfortable. As an example, a strong assist torque for increasing the ankle angle may be provided at a timing when the impaired leg is required to perform the push-off. The timing may be determined by directly determining a gait state of the impaired leg. As another example, the timing may be determined by indirectly determining a gait state of the impaired leg based on a gait state of a normal leg.

According to an aspect, the gait state of the normal leg may be determined based on a leg image generated by a camera attached to the impaired leg. A method for providing an assist torque to the impaired leg based on a leg image generated by capturing the normal leg and a walking assistance device performing the method will be described in detail with reference to FIGS. 5 through 19.

Figure 5:
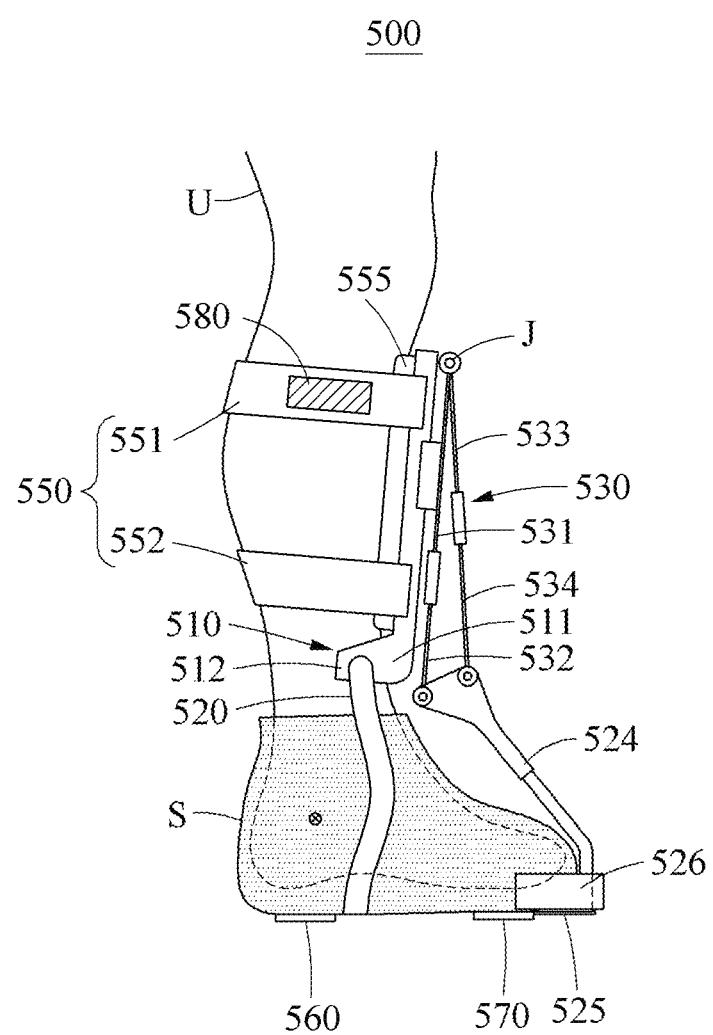
FIG. 5 illustrates an ankle-type walking assistance device according to at least one example embodiment.

FIG. 5 illustrates an ankle-type walking assistance device according to at least one example embodiment.

A walking assistance device 500 may be an ankle exoskeleton device, and may be a wearable device.

The walking assistance device 500 may assist a push-off motion of a leg of a user. In the push-off or toe-off motion, a stance leg of the user may be almost fully stretched. At this time, a motion of stretching an ankle may have an effect of pushing a center of mass of the user forward. The walking assistance device 500 may assist walking of the user by applying an assist torque for stretching the ankle.

As an example, the walking assistance device 500 may apply the assist torque for stretching the ankle by interacting with a sole and a lower leg, and a method of applying the assist torque is not limited to the example. As another example, the walking assistance device 500 may apply the assist torque for stretching the ankle by interacting with a ground and the lower leg.

The walking assistance device 500 may include a frame 510, a sole support 520, a driving device 530, a pusher 524, a support 525, a cover 526, a wearable band 550, a cushion 555, a plurality of pressure sensors, for example, a first pressure sensor 560 and a second pressure sensor 570, and a processor (not shown).

The frame 510 may be disposed on a lower leg. For example, the frame 510 may be mounted on a front side of the lower leg, that is, a shin, or mounted on a side of the lower leg, however, example embodiments are not limited thereto. For example, the frame 510 may be mounted on a rear side of the lower leg, that is, a calf. The frame 510 may support the driving device 530. The frame 510 may include a frame body 511 and a frame extension portion 512. The frame body 511 may be mounted on a lower leg of a user. The frame body 511 may have an elongated shape in a longitudinal direction of the lower leg. The frame body 511 may have a shape corresponding to a shape of the lower leg, and may cover at least a portion of the lower leg. An inner surface of the frame body 511 may face the user, and the driving device 530 may be disposed on an outer surface of the frame body 511.

The frame extension portion 512 may extend to cover the lower leg from the frame body 511. For example, when the frame body 511 is mounted on the front side of the lower leg, the frame extension portion 512 may be formed to extend backward from the frame body 511.

Although FIG. 5 illustrates that the sole support 520 has a band shape to enclose a foot, example embodiments are not limited thereto. The sole support 520 may have all shapes to support a sole. For example, the sole support 520 may have a shape of "L" that includes a first part extending downward from the frame 510 and a second part that extends in a direction intersecting the first part and that supports a sole of a user. For example, the first part may be a strap formed of a flexible material, for example, fabric, that has a relatively low elasticity or does not have an elasticity, and the second part may be a plate formed of a rigid material, for example, plastic or metal.

The sole support 520 may have a length that is adjustable using various schemes, for example, a buckle or a snap button. The sole support 520 may easily enclose shoes with any shape. In the above structure, the length of the sole support 520 may be adjusted based on a push-off state in which a plantar-flexion angle is maximized. In this example, the sole support 520 may be relatively loosened because a force is not applied in a dorsi-flexion motion, although the sole support 520 may be tightened because a force is applied in a push-off motion. In the above structure, the walking assistance apparatus 500 may assist walking so that a push-off motion is made while a foot of a user is maintained at a natural angle.

The driving device 530 may be disposed on the frame 510. The driving device 530 may include a first guide 531, a first rod 532, a second guide 533, and a second rod 534. The first guide 531 may be fixed to the frame 510. The first guide 531 may guide a movement direction of the first rod 532. The first rod 532 may perform a translation in one degree of freedom (DOF) with respect to the first guide 531. For example, the first rod 532 may slide along an inner wall or outer wall of the first guide 531. The first rod 532 may be connected to a first portion of the pusher 524.

The second guide 533 may be rotatably connected to the frame 510. For example, the second guide 533 may be rotatably connected to a joint J disposed on the frame 510. A relative angle between the second guide 533 and the first guide 531 may be changed. The second rod 534 may perform a translation in one DOF with respect to the second guide 533. For example, the second rod 534 may slide along an inner wall or outer wall of the second guide 533. The second rod 534 may be connected to a second portion of the pusher 524. The second portion of the pusher 524 may be farther away from the frame 510 than the first portion of the pusher 524.

The driving device 530 may generate a power to operate the pusher 524 in various ways. For example, the pusher 524 may be adjustable in length and a driving method of the pusher 524 is not limited to the examples set forth herein. The pusher 524 may include a first sub-pusher and a second sub-pusher. The first sub-pusher may be connected to the first rod 532 and the second rod 534 so as to operate. The second sub-pusher may slide along an inner wall and/or an outer wall of the first sub-pusher. A user may adjust the length of the pusher 524 by adjusting a relative location of the second sub-pusher with respect to the first sub-pusher. The length of the pusher 524 may be adjusted based on a length of a foot of the user.

The support 525 may be connected to the pusher 524 and extend backward from the pusher 524, to support toes of the user. The support 525 may support the toes that are in a swing phase, to inhibit (or, alternatively, prevent) the user from falling. For example, the support 525 may be more flexible than the pusher 524. The support 525 may be deformed while the user makes a push-off motion, and accordingly the user may feel enhanced wearability. Depending on an example, the support 525 may extend further toward a sole.

The wearable band 550 may fasten the frame 510 on the lower leg of the user. For example, the wearable band 550 may include a first wearable band 551 and a second wearable band 552 that are separated in a longitudinal direction of the lower leg. For example, the first wearable band 551 and the second wearable band 552 may be disposed on opposite sides of a thickest portion of the calf of the user. The first wearable band 551 may inhibit (or, alternatively, prevent) the frame 510 from being upwardly detached from the user, and the second wearable band 552 may inhibit (or, alternatively, prevent) the frame 510 from being downwardly detached from the user.

The cushion 555 may be disposed on a rear side of the frame 510, to reduce an impact applied from the frame 510 to the user while the sole of the user is pushing the ground.

The cover 526 may be connected to the pusher 524 and extend backward from the pusher 524, to cover a portion of a side of the foot of the user.

The plurality of pressure sensors 560 and 570 may be arranged in different areas of the sole of the user and measure a pressure generated between the ground and the sole. For example, the first pressure sensor 560 may be disposed in a backward portion of the sole and the second pressure sensor 570 may be disposed in a forward portion of the sole. The first pressure sensor 560 and the second pressure sensor 570 may be located on the support 525 having extended toward the sole.

A camera 580 may capture a leg from another leg on which the walking assistance device 500 is worn. Although FIG. 5 illustrates that the camera 580 is attached to the first wearable band 551, a position of the camera 580 is not limited to the examples set forth herein.

The processor may calculate an assist torque value to be output to the other leg based on an image captured by the camera 580 and control the driving device 530 such that the calculated assist torque value is output.

Figure 6:
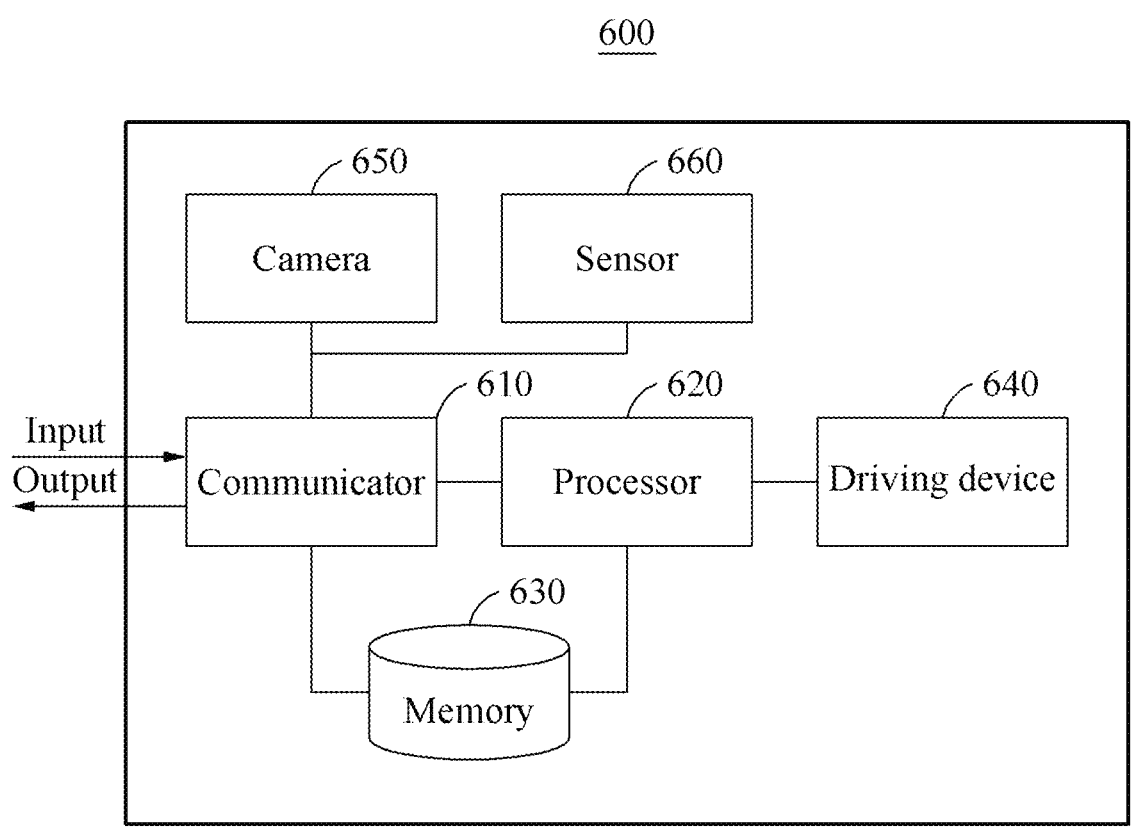
FIG. 6 is a block diagram illustrating a walking assistance device according to at least one example embodiment.

FIG. 6 is a block diagram illustrating a walking assistance device according to at least one example embodiment.

A walking assistance device 600 includes a communicator 610, a processor 620, a memory 630, a driving device 640, a camera 650, and a sensor 660. The walking assistance device 600 may correspond to an electronic device of the walking assistance device 500 of FIG. 5.

The communicator 610 may be connected to the processor 620, the memory 630, the camera 650, and the sensor 660 to transmit and receive data. The communicator 610 may be connected to an external device to transmit and receive data.

Hereinafter, transmitting and receiving "A" may represent transmitting and receiving "information or data that indicates A".

The communicator 610 may be configured as a circuitry within the walking assistance device 600. For example, the communicator 610 may include an internal bus and an external bus. As another example, the communicator 610 may refer to an element that connects the walking assistance device 600 and the external device. The communicator 610 may be an interface. The communicator 610 may receive data from the external device and transmit the data to the processor 620 and the memory 630.

The processor 620 may process data received by the communicator 610 and data stored in the memory 630. Here, the processor 620 may be a data processing device embodied by hardware including a circuitry having a physical structure to execute desired operations. The operations may include, for example, codes and instructions included in a program. The data processing device embodied by hardware may include, for example, a microprocessor, a central processing unit (CPU), a processor core, a multi-core processor, a multiprocessor, an application-specific integrated circuit (ASIC), and a field programmable gate array (FPGA).

The processor 620 may execute a computer-readable code, for example, software, stored in a memory, for example, the memory 630 and instructions caused by the processor 620.

The memory 630 may store data received by the communicator 610 and data processed by the processor 620. For example, the memory 630 may store the program. The stored program may be a set of syntaxes that are coded and executable by the processor 620 to assist walking of the user.

For example, the memory 630 may store instructions that, when executed by processing circuitry included in, for example, the processor 620, configure the processor 620 as a special purpose computer to calculate an assist torque value to be output to the other leg based on an image captured by the camera 580 and control the driving device 530 such that the calculated assist torque value is output.

The memory 630 may include, for example, at least one volatile memory, nonvolatile memory, random memory access (RAM), flash memory, a hard disk drive, and an optical disk drive.

The memory 630 may store an instruction set, for example, software, for operating the walking assistance device 600. The instruction set for operating the walking assistance device 600 may be executed by the processor 620.

The driving device 640 may include mechanical devices configured to adjust an angle of an ankle of the user. For example, the driving device 640 may include a motor, and a torque output from the motor may be used to adjust the angle of the ankle.

The camera 650 may be attached to the walking assistance device 600 to capture a leg from another leg on which the walking assistance device 600 is worn. For example, the camera 650 may be disposed such that a side view of the second leg always appears in a captured image.

The sensor 660 may include at least one pressure sensor. For example, the sensor 660 may include the first pressure sensor 560 and the second pressure sensor 570 of FIG. 5. The pressure sensor may convert a magnitude of pressure applied to the pressure sensor to a voltage and output the voltage.

The communicator 610, the processor 620, the memory 630, the driving device 640, the camera 650, and the sensor 660 will be further described with reference to FIGS. 7 through 19.

Figure 7:
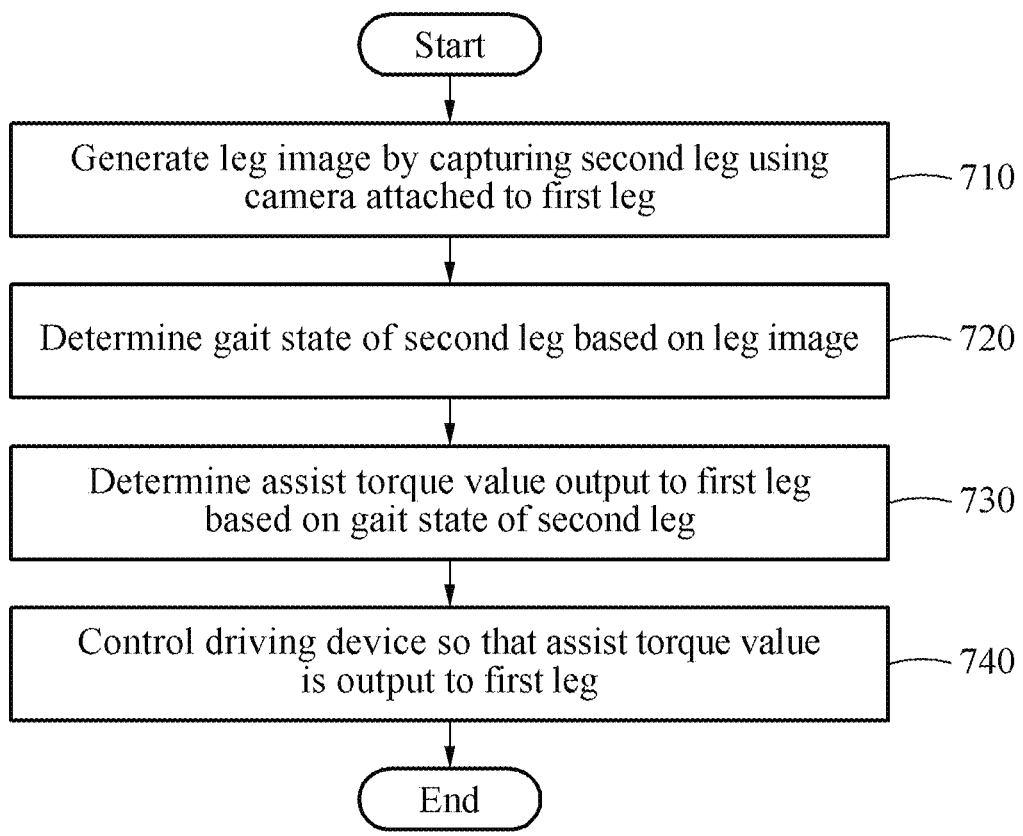
FIG. 7 is a flowchart illustrating a method of controlling a driving device of a walking assistance device according to at least one example embodiment.

FIG. 7 is a flowchart illustrating a method of controlling a driving device of a walking assistance device according to at least one example embodiment.

Operations 710 through 740 may be performed by the processor 620 of FIG. 6.

In operation 710, the processor 620 generates a leg image by capturing a second leg using the camera 650 attached to a first leg. The camera 650 may be, for example, a camera for generating a color image. The camera 650 may include a lens for securing a wide angle of view. The camera 650 may also be a thermal imaging camera for generating a thermal image. The thermal imaging camera may generate an image of the second leg even when the thermal imaging camera is covered by clothes.

In operation 720, the processor 620 determines a gait state of the second leg based on the leg image. The gait state of the second leg may be represented by a degree of process of a gait cycle. The degree of process of the gait cycle may be expressed as a percentage (%).

A method of determining a gait state of the second leg will be further described with reference to FIGS. 11 through 17.

In operation 730, the processor 620 determines an assist torque value output to the first leg based on the gait state of the second leg. As an example, the assist torque value output to the first leg may be determined based on an assist torque table or an assist torque trajectory mapped to the gait state of the second leg. As another example, a gait state of the first leg corresponding to the gait state of the second leg may be determined, so that the assist torque value output to the first leg is determined based on an assist torque table or an assist torque trajectory mapped to the determined gait state of the first leg.

In operation 740, the processor 620 controls the driving device 640 so that the assist torque value is output to the first leg. Mechanical elements of the driving device 640 may be controlled so that the assist torque is output.

Figure 8:
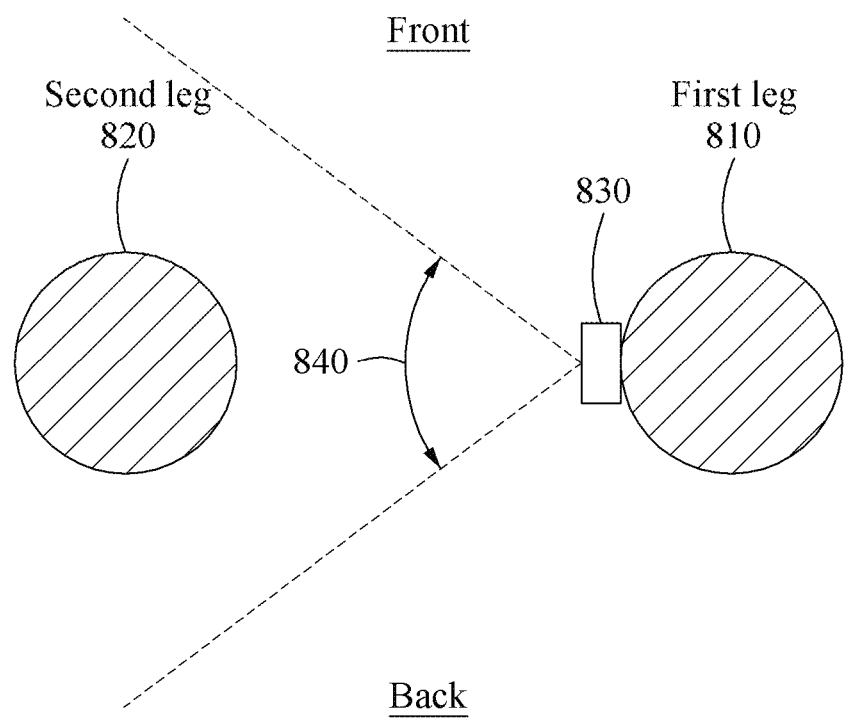
FIG. 8 illustrates a method of capturing a second leg using a camera attached to a first leg according to at least one example embodiment.

FIG. 8 illustrates a method of capturing a second leg using a camera attached to a first leg according to at least one example embodiment.

When a first leg 810 is an impaired leg, a walking assistance device 600 may be worn on the first leg 810. A camera 830 of the walking assistance device 600 may be attached to the first leg 810 to capture a side view of a second leg 820 which is a normal leg. For example, a position of the camera 830 may be determined such that the second leg 820 is included in an angle of view 840 of the camera 830. The camera 830 may include a lens of which the angle of view 840 is relatively large.

Figure 9:
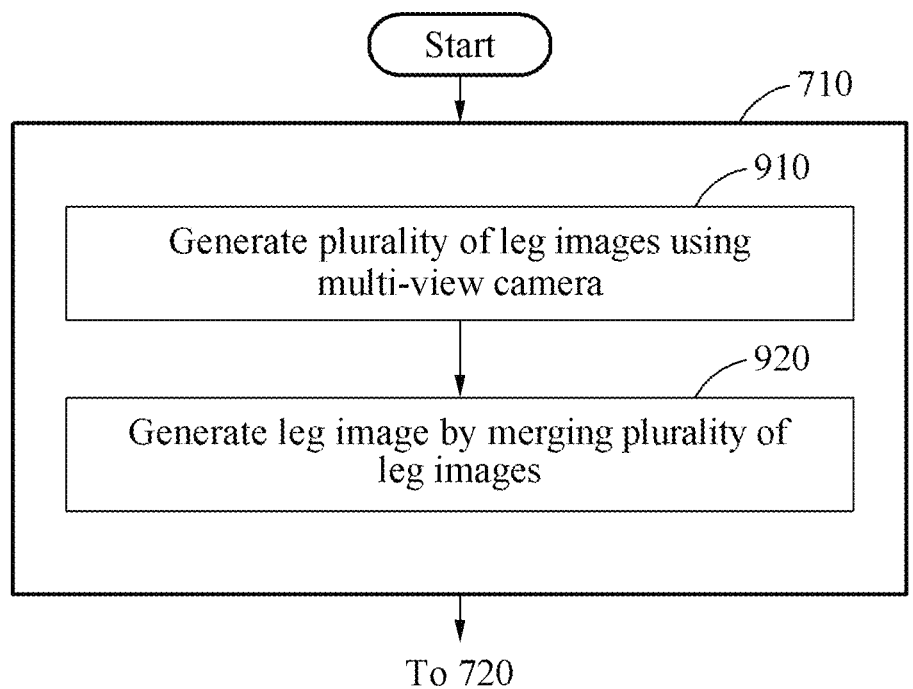
FIG. 9 is a flowchart illustrating a method of generating an image according to at least one example embodiment.

FIG. 9 is a flowchart illustrating a method of generating an image according to at least one example embodiment.

According to an aspect, operation 710 of FIG. 7 may include operations 910 and 920. The following example embodiment relates to a method of generating a leg image in a case in which the camera 650 is a multi-view camera.

In operation 910, the processor 620 generates a plurality of leg images using the multi-view camera. The multi-view camera may include a plurality of lenses and generate a leg image for each of the lenses. The generated leg images may be images corresponding to the same viewpoint. The plurality of lenses may be in an array.

In operation 920, the processor 620 generates a leg image by merging the plurality of leg images.

Figure 10:
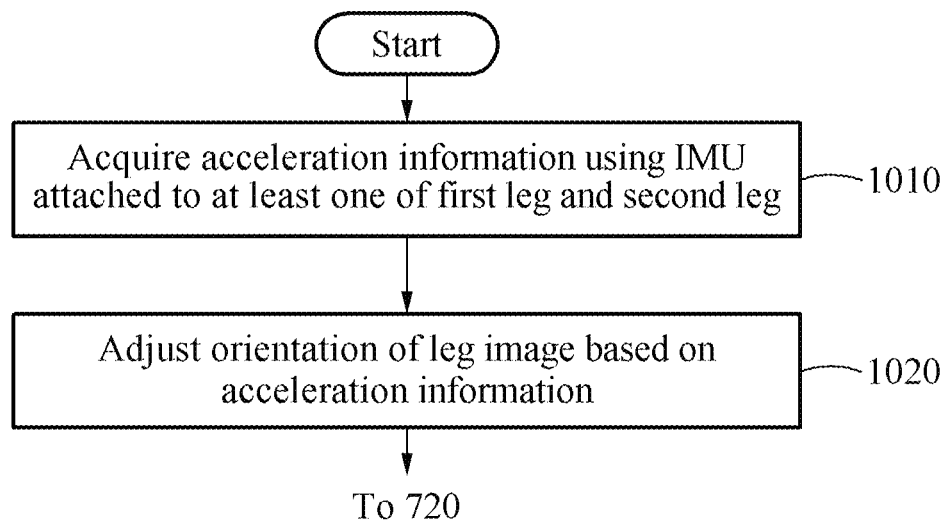
FIG. 10 is a flowchart illustrating a method of adjusting an orientation of an image according to at least one example embodiment.

FIG. 10 is a flowchart illustrating a method of adjusting an orientation of an image according to at least one example embodiment.

Since a first leg moves during walking, a pose of the camera 650 may be changed. When the pose of the camera 650 is changed, an orientation of a captured leg image may also be changed. For example, even when a user walks on a flat surface, a ground may not parallel to a horizontal axis of a leg image but may appear to be inclined in the leg image. An actual ground surface may be detected by adjusting an orientation of the leg image. The ground state may be an actual gradient.

In operation 1010, the processor 620 acquires at least one of acceleration information and orientation information using an inertial measurement unit (IMU) attached to at least one of a first leg and a second leg. The orientation information may include a roll, a pitch, and a yaw. When the camera 650 and the IMU are attached to the same rigid body, the acceleration information and the orientation information may be associated with the camera 650. A point in time at which the acceleration information and the orientation information are generated may be the same as a point in time at which an initial leg image is generated. For example, operation 1010 may be performed simultaneously with operation 710.

In operation 1020, the processor 620 adjusts an orientation of the leg image based on the acceleration information and the orientation information. For example, the processor 620 may calculate an angle at which the camera 650 rotates relative to the ground based on the acceleration information and the orientation information and reversely rotate the leg image by the angle, thereby adjusting the orientation of the leg image. The leg image having the adjusted orientation may be used in operation 720.

Figure 11:
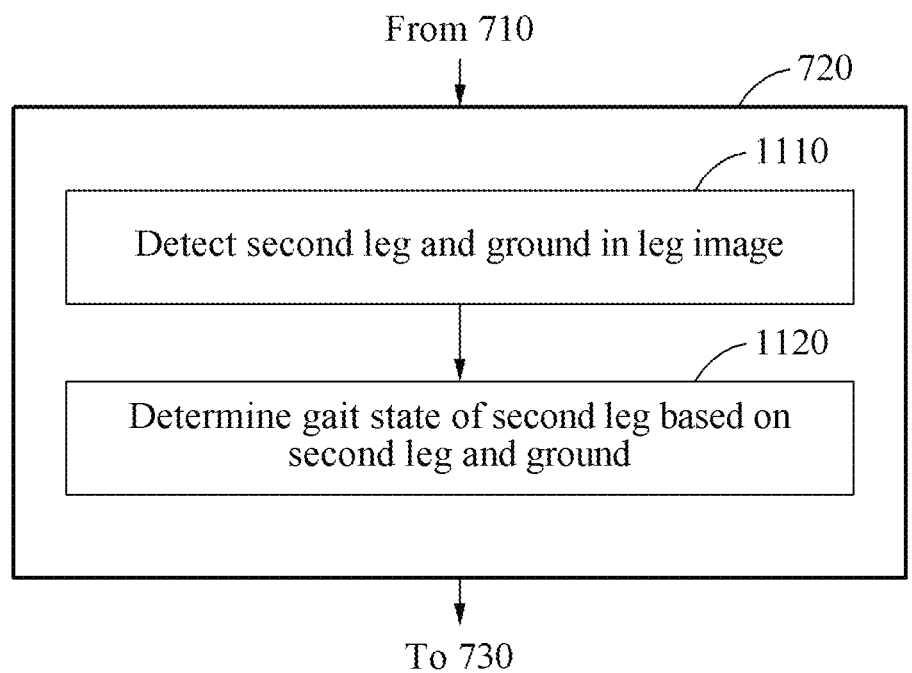
FIG. 11 is a flowchart illustrating a method of determining a gait state of a second leg image according to at least one example embodiment.

FIG. 11 is a flowchart illustrating a method of determining a gait state of a second leg image according to at least one example embodiment.

According to an aspect, operation 720 of FIG. 7 may include operations 1110 and 1120.

In operation 1110, the processor 620 detects a second leg and a ground in a leg image. The processor 620 may remove a background except the second leg and the ground in the leg image. The second leg and the background may be separated using a threshold of a pixel brightness value of the leg image.

In operation 1120, the processor 620 determines a gait state of the second leg based on the second leg and the ground. For example, an angle between the ground and the second leg may be used to determine the gait state of the second leg. The angle between the ground and the second leg may be associated with a gait state corresponding to an angle of the second leg.

A method of determining a gait state of the second leg based on the ground and the second leg will be further described with reference to FIGS. 12 through 17.

Figure 12:
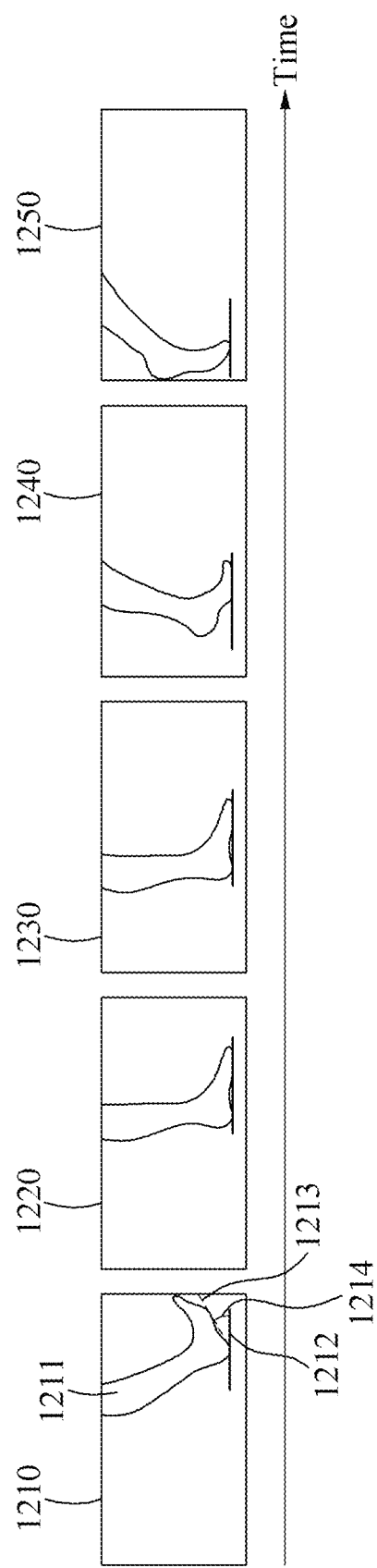
FIG. 12 illustrates leg images in a case in which a second leg is in a stance state image according to at least one example embodiment.

FIG. 12 illustrates leg images in a case in which a second leg is in a stance state image according to at least one example embodiment.

In leg images 1210 through 1250, since a second leg is in contact with a ground, it is determined that the second leg is in a stance state. To classify the stance state, an angle 1214 between a second leg 1211, for example, a sole 1213 and a ground 1212 may be determined.

Figure 13:
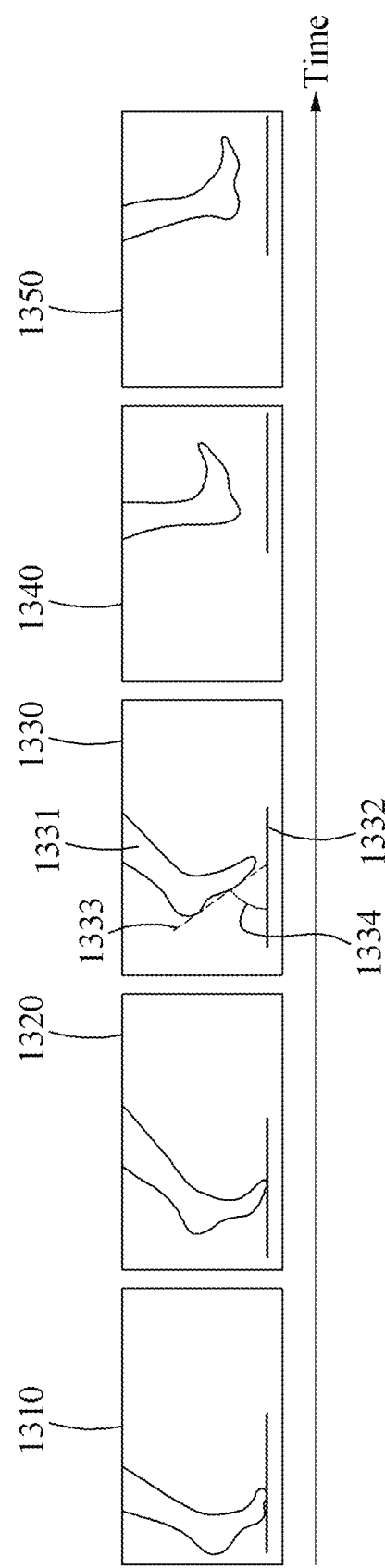
FIG. 13 illustrates leg images in a case in which a second leg is in a stance state image according to at least one example embodiment.

FIG. 13 illustrates leg images in a case in which a second leg is in a stance state image according to at least one example embodiment.

In leg images 1310 through 1350, since a second leg is separated from a ground, it is determined that the second leg is in a swing state. To classify the swing state, an angle 1334 between a second leg 1331, for example, a sole 1333 and a ground 1332 may be determined.

Figure 14:
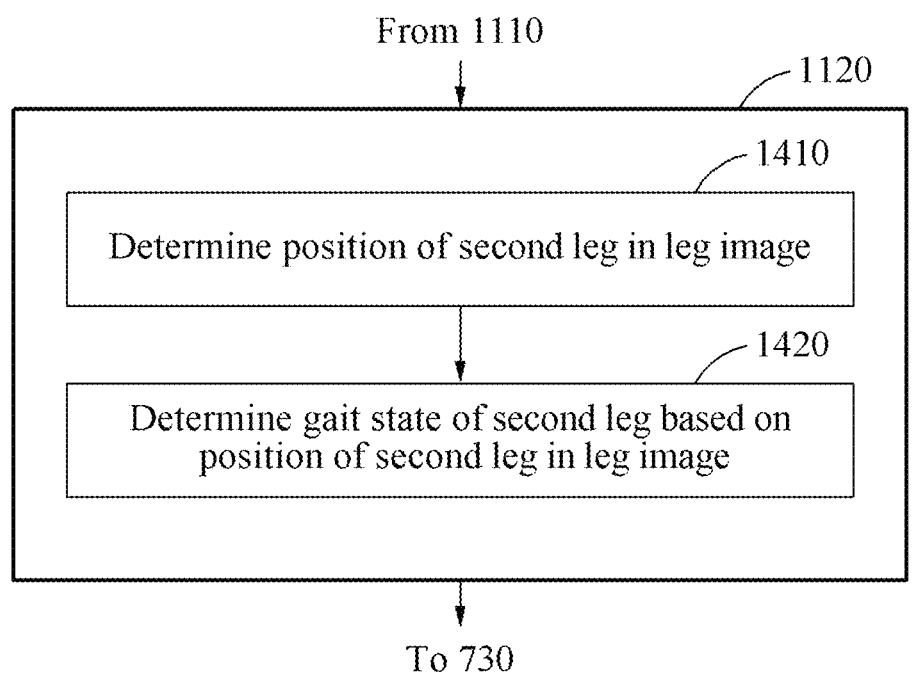
FIG. 14 is a flowchart illustrating a method of determining a gait state based on a position of a second leg image according to at least one example embodiment.

FIG. 14 is a flowchart illustrating a method of determining a gait state based on a position of a second leg image according to at least one example embodiment.

According to an aspect, operation 1120 of FIG. 11 may include operations 1410 and 1420.

In operation 1410, the processor 620 determines a position of a second leg in a leg image. For example, the position of the second leg may be an x-axial coordinate value and a y-axial coordinate value in an image.

In operation 1420, the processor 620 determines a gait state of the second leg based on the position of the second leg in the leg image. A method of determining a gait state of the second leg based on the position of the second leg in the leg image will be further described with reference to FIGS. 15 through 17.

Figure 15:
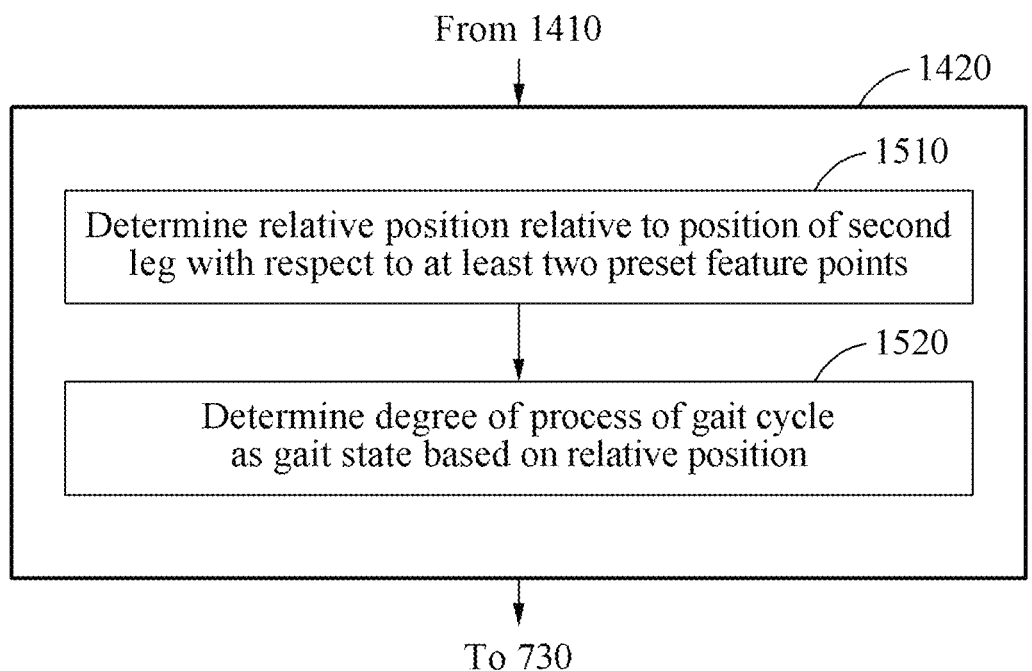
FIG. 15 is a flowchart illustrating a method of determining a degree of process of a gait cycle as a gait state based on a relative position relative to a position of a second leg according to at least one example embodiment.

FIG. 15 is a flowchart illustrating a method of determining a degree of process of a gait cycle as a gait state based on a relative position relative to a position of a second leg according to at least one example embodiment.

According to an aspect, operation 1420 of FIG. 14 may include operations 1510 and 1520.

In operation 1510, the processor 620 determines a relative position relative to a position of a second leg with respect to at least two desired (or, alternatively preset) feature points. For example, the at least two feature points may be a leftmost position and a rightmost position of the second leg appearing during walking. In order for the relative position relative to the position of the second leg with respect to the two feature positions to be determined, all leg images need to contain the same portion.

In operation 1520, the processor 620 determines a degree of process of a gait cycle as a gait state based on the relative position relative to the second leg with respect to the at least two feature positions.

Figure 16:
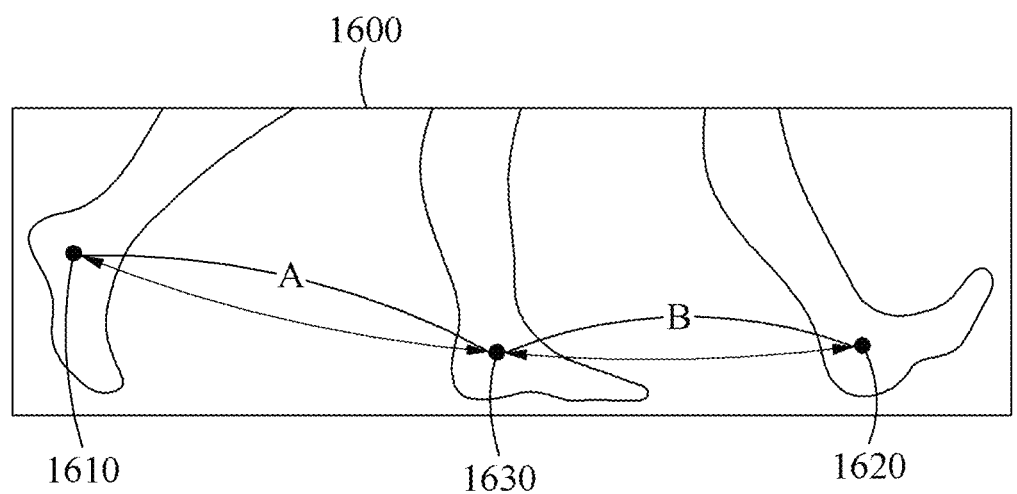
FIG. 16 illustrates a relative position relative to a position of a second leg with respect to desired (or, alternatively preset) positions according to at least one example embodiment.

FIG. 16 illustrates a relative position relative to a position of a second leg with respect to desired (or, alternatively preset) positions according to at least one example embodiment.

An algorithm for determining a gait state based on data on an actual gait state and leg images acquired in a previously performed gait process may be learned. The algorithm for determining a gait state may be, for example, a neural network. The data on an actual gait state may include acceleration information acquired by an IMU and a pressure value acquired by a pressure sensor.

In an image 1600 obtained by merging leg images of a second leg for one gait cycle, a leftmost position 1610 and a rightmost position 1620 of the second leg may be shown. The image 1600 may be acquired in the previously performed gait process. When the second leg is at the leftmost position 1610, for example, in a heel strike motion, a degree of process of the gait cycle may be determined to be 0%. When the second leg is at the rightmost position 1620, for example, in a push-off motion, a degree of process of the gait cycle may be determined to be 60%.

As an example, when a current position 1630 of the second leg is determined based on a leg image acquired in a process of a stance state, a degree of process of the gait cycle may be determined to be "B/(A+B)×60(%)".

As another example, when the current position 1630 of the second leg is determined based on a leg image acquired in a process of a swing state, a degree of process of the gait cycle may be determined to be "(A/(A+B)×40)+60(%)".

Figure 17:
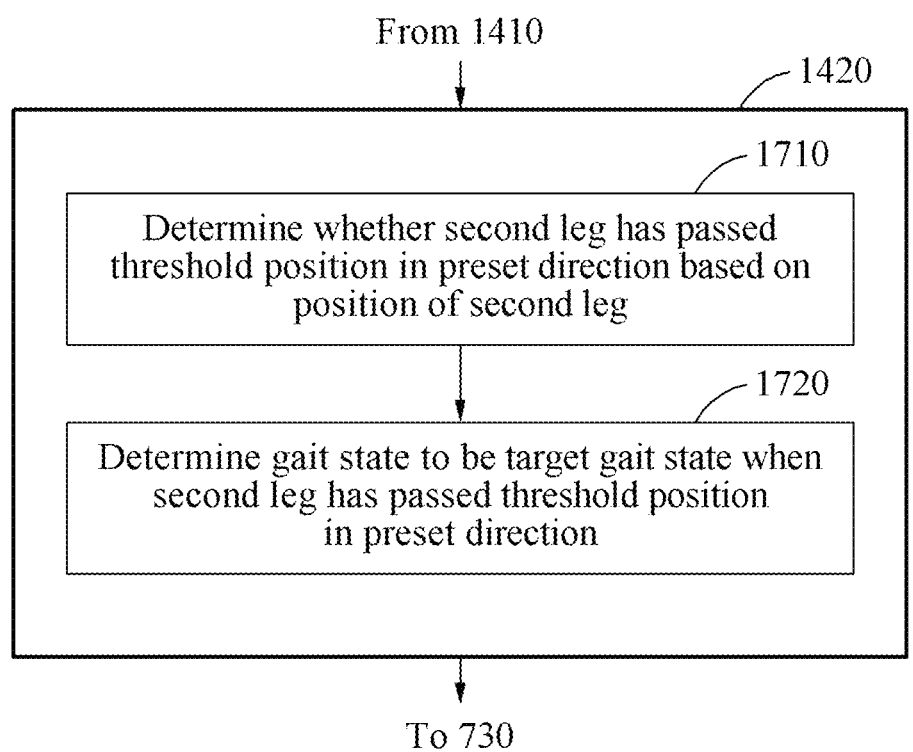
FIG. 17 is a flowchart illustrating a method of determining a gait state of a second leg when the second leg has passed a threshold position in a desired (or, alternatively preset) direction according to at least one example embodiment.

FIG. 17 is a flowchart illustrating a method of determining a gait state of a second leg when the second leg has passed a threshold position in a desired (or, alternatively preset) direction according to at least one example embodiment.

According to an aspect, operation 1420 of FIG. 14 may include operations 1710 and 1720.

In operation 1710, the processor 620 determines whether a second leg has passed a threshold position in a desired (or, alternatively preset) direction based on a position of the second leg. As an example, the threshold position may be a leg position indicating that a center of mass of a user moves forward. As another example, the threshold position may be a leg position corresponding to a terminal stance state.

In operation 1720, the processor 620 determines a gait state of the second leg to be a target gait state when it is determined that the second leg has passed the threshold position in the desired (or, alternatively preset) direction.

When the gait state of the second leg is determined to be the target gait state, in operation 730, the processor 620 determines an assist torque value output to a first leg based on the target gait state. As an example, when the gait state of the second leg is the target gait state, an assist torque value for push-off of the first leg may be determined. As another example, when the gait state of the second leg is the target gait state, an assist torque value for dorsiflexion of the first leg may be determined.

Figure 18:
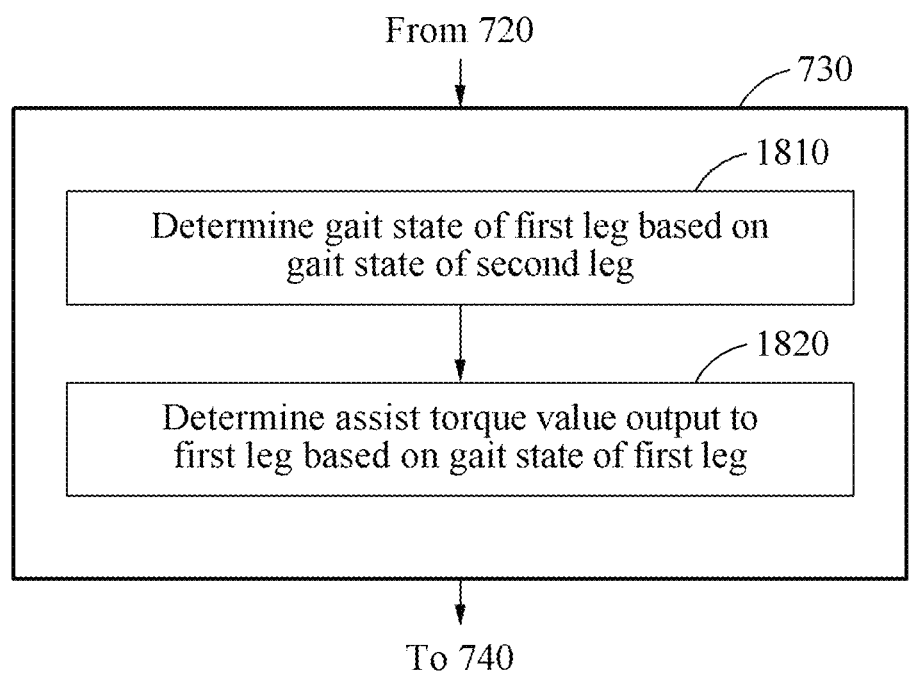
FIG. 18 is a flowchart illustrating a method of determining an assist torque value output to a first leg based on a gait state of the first leg according to at least one example embodiment.

FIG. 18 is a flowchart illustrating a method of determining an assist torque value output to a first leg based on a gait state of the first leg according to at least one example embodiment.

According to an aspect, operation 730 of FIG. 7 may include operations 1810 and 1820.

In operation 1810, the processor 620 determines a gait state of a first leg based on a gait state of a second leg. According to a general gait mechanism, since the first leg and the second leg symmetrically operates at regular intervals, a current gait state of the first leg corresponding to a current gait state of the second leg may be determined.

In operation 1820, the processor 620 determines an assist torque value output to the first leg based on the gait state of the first leg. For example, the assist torque value may be determined based on an ankle torque trajectory as shown in FIG. 4.

Figure 19:
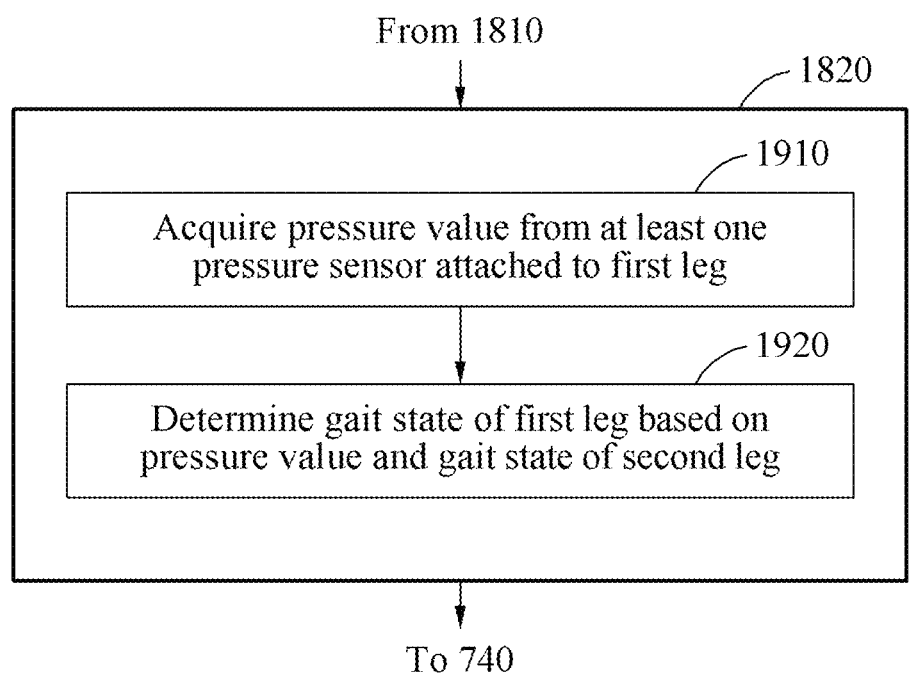
FIG. 19 is a flowchart illustrating a method of determining a gait state of a first leg based on a pressure value of the first leg and a gait state of a second leg according to at least one example embodiment.

FIG. 19 is a flowchart illustrating a method of determining a gait state of a first leg based on a pressure value of the first leg and a gait state of a second leg according to at least one example embodiment.

According to an aspect, operation 1830 of FIG. 18 may include operations 1910 and 1920.

In operation 1910, the processor 620 acquires a pressure value from at least one pressure sensor attached to a first leg. For example, pressure values may be acquired from the first pressure sensor 560 and the second pressure sensor 570 of FIG. 5.

In operation 1920, the processor 620 determines a gait state of the first leg based on the pressure value and a gait state of a second leg.

As an example, when a gait state of the second leg is a stance state and a pressure value acquired from the first pressure sensor 560 disposed at a rear part of the first leg is greater than a threshold, the gait state of the first leg may be determined or updated based on a degree of process of a gait cycle corresponding to a heel strike. As another example, when a gait state of the second leg is a swing state and pressure values acquired from the first pressure sensor 560 disposed at a rear part of the first leg and the second pressure sensor 570 disposed at a front part of the first leg are greater than a threshold, the gait state of the first leg may be determined based on a degree of process of a gait cycle corresponding to a middle stance.

A hip-type walking assistance device 2000, which may be additionally combined with the walking assistance device 600 described with reference to FIGS. 6 through 19, will be described with reference to FIGS. 20 and 21. The hip-type walking assistance device 2000 may be a device for providing a gait assist torque to a hip joint of a user. The walking assistance device 600 may be connected to the hip-type walking assistance device 2000 through a wired or wireless communication. The hip-type walking assistance device 2000 may provide the user with an assist torque associated with a gait phase determined for a motion of the user. For example, the walking assistance device 600 may provide an assist torque to an ankle joint of the user, and the hip-type walking assistance device 2000 may provide an assist torque to the hip joint of the user.

Hereinafter, the hip-type walking assistance device will be described.

Figure 20:
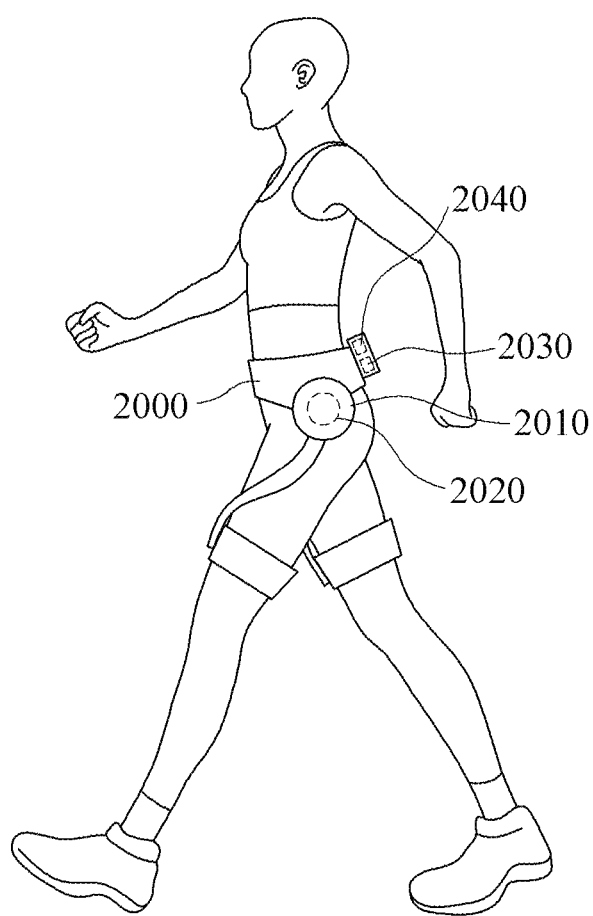
FIGS. 20 and 21 illustrate a hip-type walking assistance device according to at least one example embodiment.
Figure 21:
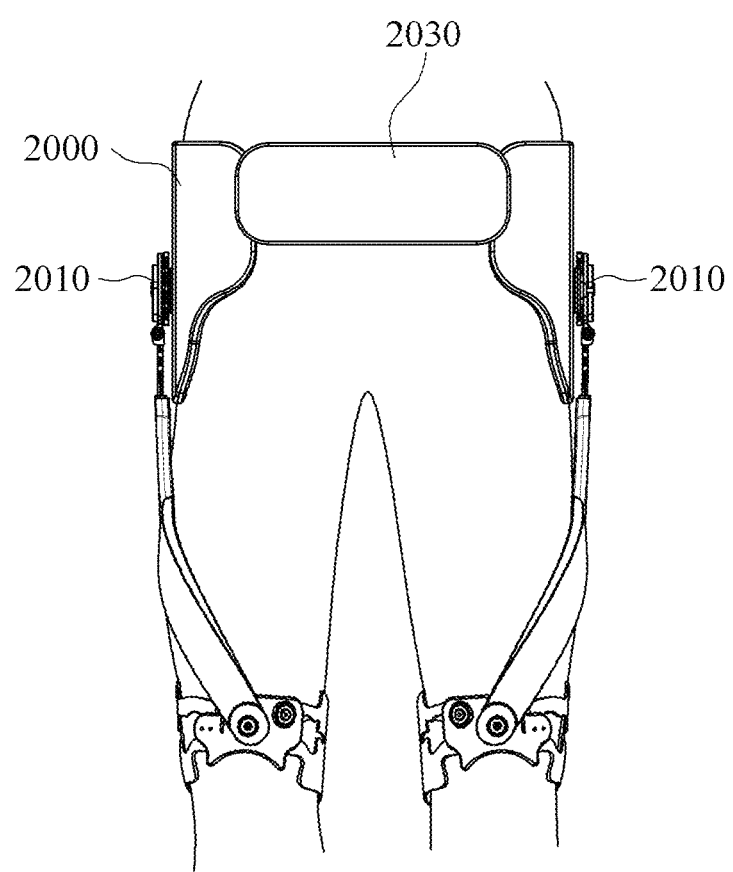

FIGS. 20 and 21 illustrate a hip-type walking assistance device according to at least one example embodiment.

Referring to FIG. 20, a hip-type walking assistance device 2000 is worn by a user and to assist walking of the user. The walking assistance device 2000 may be a wearable device.

The example embodiments of FIGS. 20 and 21 may be applicable to a hip-type but are not limited thereto. The example embodiments may be applicable to any type of devices that assist walking of the user.

According to an aspect, the hip-type walking assistance device 2000 includes a driving device 2010, a sensor 2020, an IMU 2030, and a controller 2040.

The driving device 2010 may provide a driving force to a hip joint of the user. For example, the driving device 2010 may be provided to a right hip portion and/or a left hip portion of the user. The driving device 2010 may include a motor capable of generating a rotational torque.

The sensor 2020 may measure an angle of the hip joint of the user during walking. Information associated with the angle of the hip joint of the user sensed at the sensor 2020 may include an angle of a right hip joint, an angle of a left hip joint, a difference between the angle of the right hip joint and the angle of the left hip joint, and a hip joint motion direction. For example, the sensor 2020 may be included in the driving device 2010.

The sensor 2020 may include a potentiometer. The potentiometer may sense a right (R) axis joint angle, a left (L) axis joint angle, an R axis joint acceleration, and an L axis joint acceleration according to a gait motion of the user.

The IMU 2030 may measure acceleration and posture information during walking. For example, the IMU 2030 may sense each of X axis, Y axis, and Z axis acceleration, and X axis, Y axis, and Z axis angular velocity according to a gait motion of the user.

The hip-type walking assistance device 2000 may detect a point at which a foot of the user lands based on acceleration information measured by the IMU 2030.

In addition to the sensor 2020 and the IMU 2030, the hip-type walking assistance device 2000 may include other sensors, for example, an electromyogram (EMG) sensor and an electroencephalogram (EEG) sensor capable of sensing a change in biosignals or momentum of the user according to the gait motion of the user.

The controller 2040 may control the driving device 2010 to output an assistance force to assist walking of the user. For example, the hip-type walking assistance device 2000 may include two driving devices 2010 on a left hip and a right hip of the user, respectively, and the controller 2040 may output control signals for controlling the two driving devices 2010 to generate a torque. The controller 2040 may include a communicator, a processor, and a memory.

The driving device 2010 may generate a torque in response to the control signal output from the controller 2040. The hip-type walking assistance device 2000 may include the driving device 2010 for a right leg of the user and the driving device 2010 for a left leg of the user. For example, the controller 2040 may be designed to control one of the driving devices 2010. When the controller 2040 controls only a single driving device 2010, a number of controllers 2040 may be provided. As another example, the controller 2040 may be designed to control all of the driving devices 2010 for the left leg and the right leg of the user.

Figure 22:
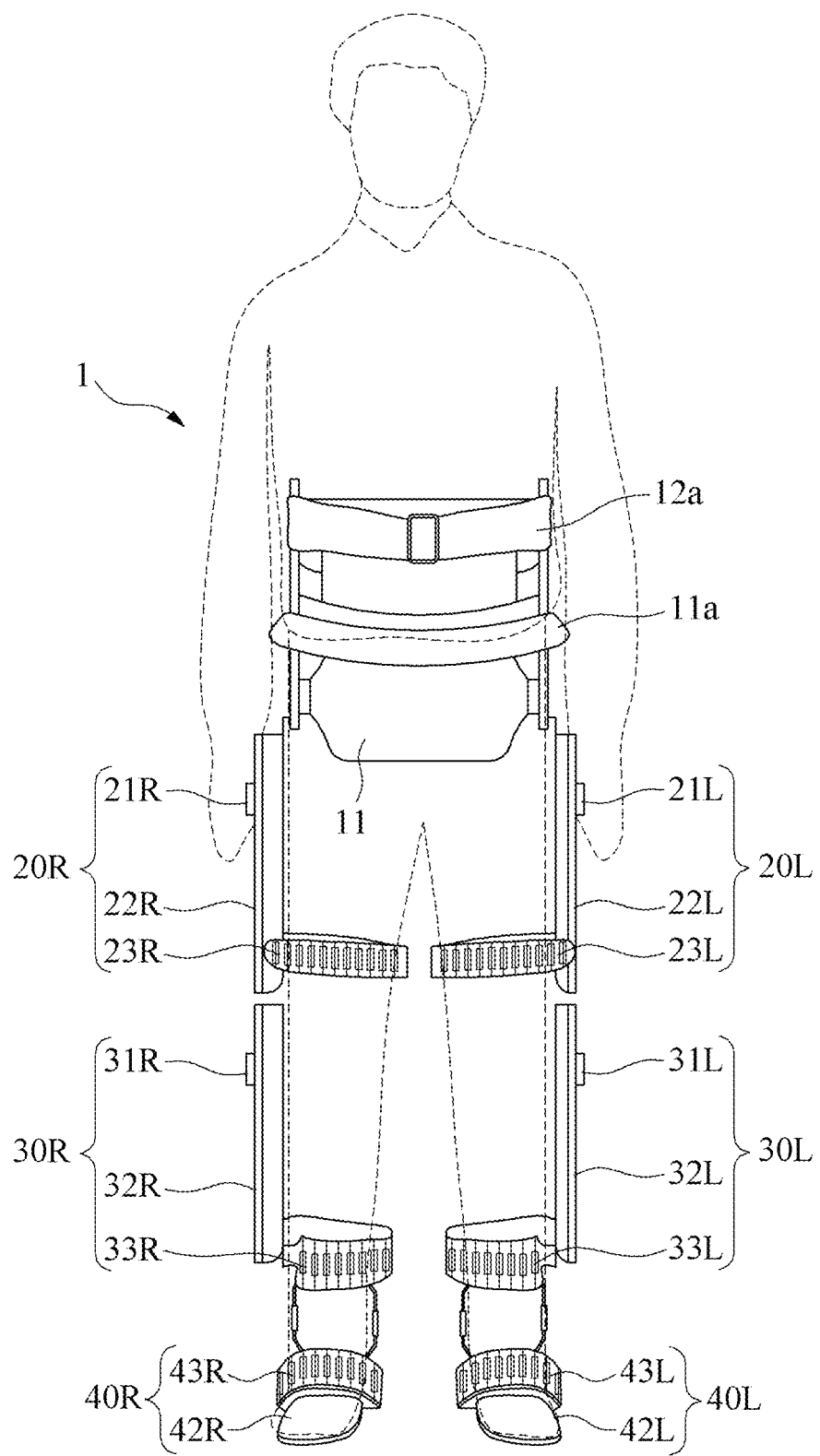
FIGS. 22 through 24 illustrate a body-type walking assistance device according to at least one example embodiment.
Figure 23:
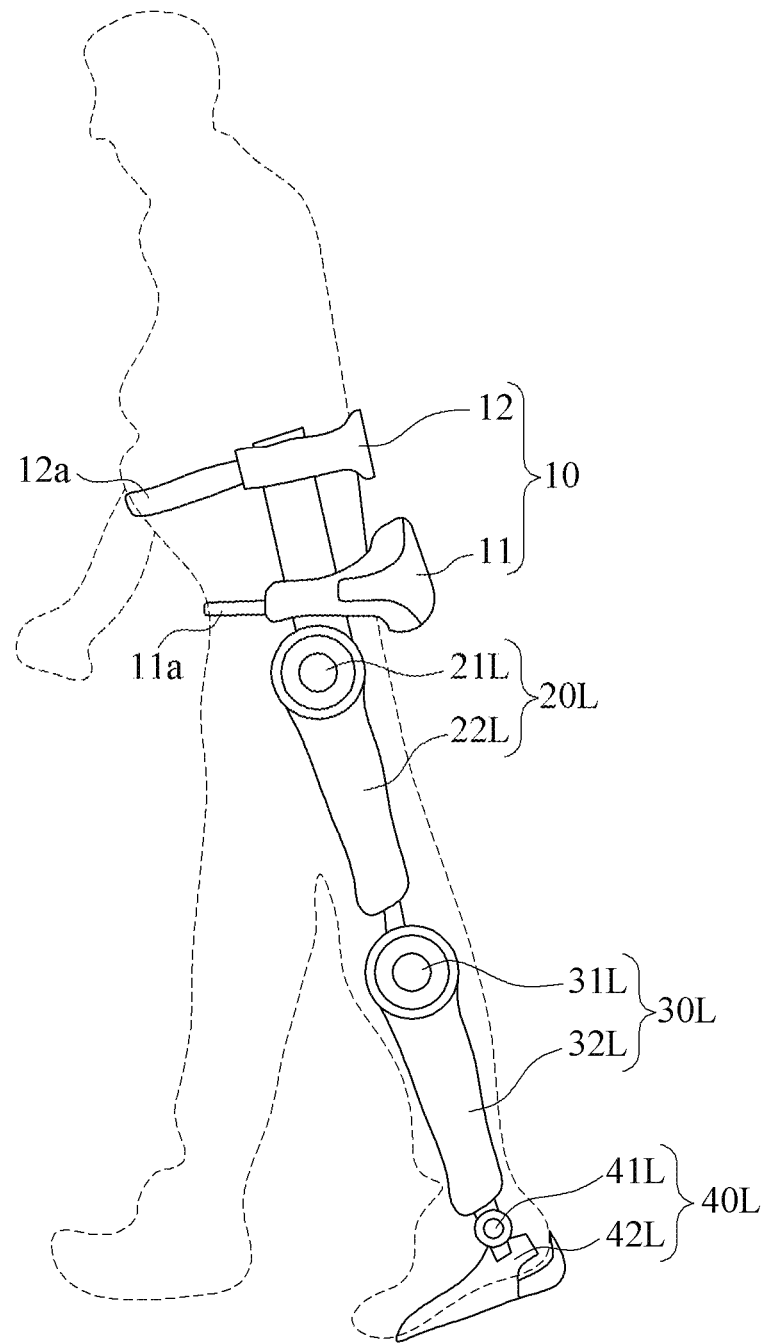
Figure 24:
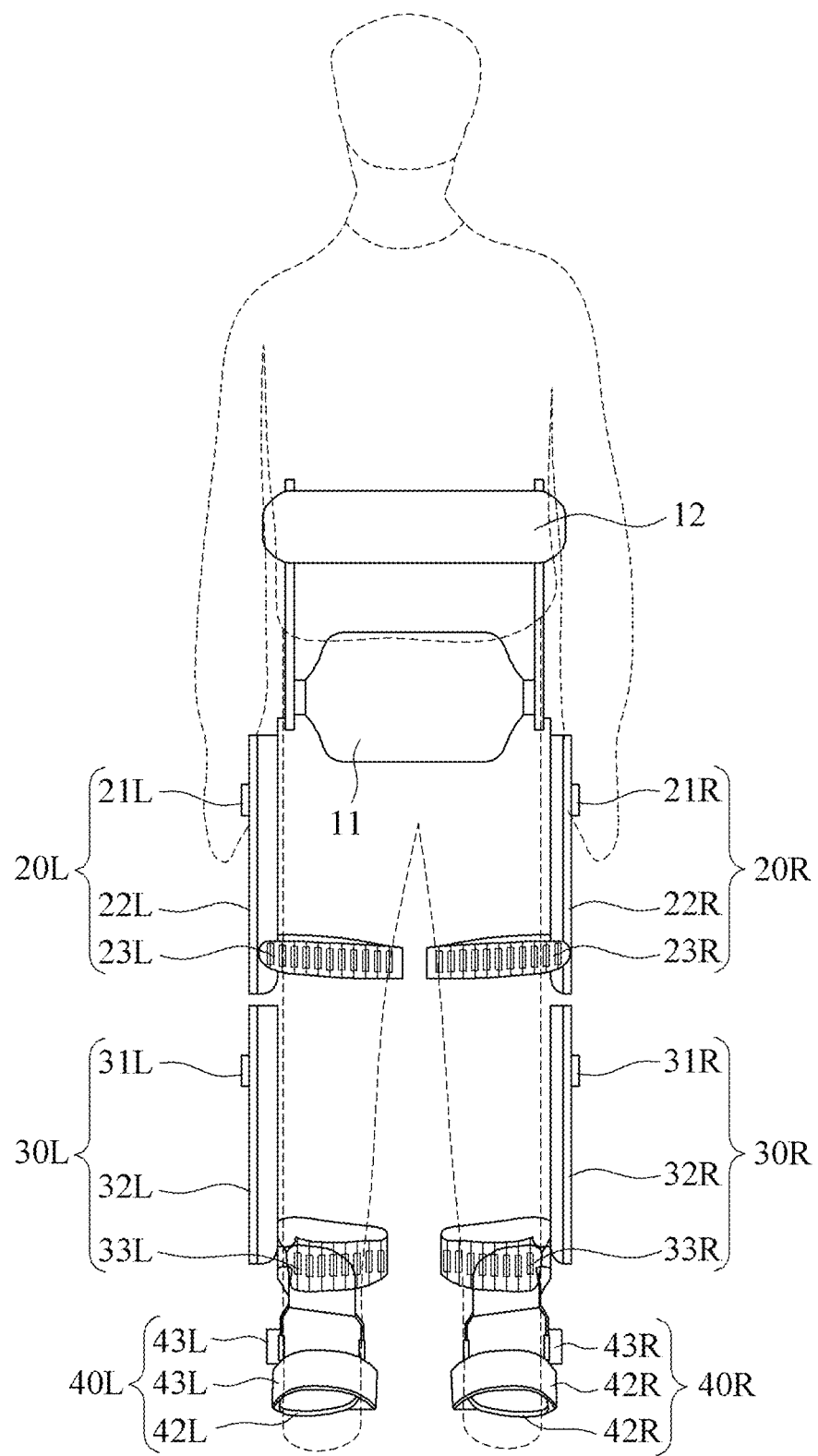

Unlike the hip-type walking assistance device 2000 of FIGS. 20 and 21, the walking assistance device 500 may be included in a body-type walking assistance device 1 of FIGS. 22 through 24. The body-type walking assistance device 1 may be a device for providing a gait assist torque to each of a hip joint, a knee joint, and an ankle joint of the user.

Hereinafter, the body-type walking assistance device will be described.

FIGS. 22 through 24 illustrate a body-type walking assistance device 1 according to at least one example embodiment. FIG. 22 is a front view of a body-type walking assistance device 1, FIG. 23 is a side view of the body-type walking assistance device 1, and FIG. 24 is a rear view of the body-type walking assistance device 1.

According to an aspect, the body-type walking assistance device 1 may include the driving device 2010, the sensor 2020, the IMU 2030, and the controller 2040.

Referring to FIGS. 22 through 24, the body-type walking assistance device 1 may be in an exoskeleton structure to be wearable to each of a left leg and a right leg of a user. The user may perform a motion, for example, an extension motion, a flexion motion, an adduction motion, and an abduction motion, with wearing the body-type walking assistance device 1. The extension motion is a movement that extends a joint, and the flexion motion is a movement that flexes a joint. The adduction motion is a movement that moves a leg to be close to a central axis of the body, and the abduction motion is a movement that extends a leg to be away from the central axis of the body.

Referring to FIGS. 22 through 24, the body-type walking assistance device 1 may include a body 10 and a mechanical part, for example, first structural parts 20R and 20L, second structural parts 30R and 30L, and third structural parts 40R and 40L.

The body 10 may include a housing 11. Various parts may be embedded in the housing 11. The parts embedded in the housing 11 may include, for example, a central processing unit (CPU), a printed circuit board (PCB), various types of storage devices, and a power source. For example, the body 10 may include the controller 2040. The controller 2040 may include the CPU and the PCB.

The CPU may be a microprocessor. The microprocessor may include an arithmetic logic operator, a register, a program counter, a command decoder and/or a control circuit in a silicon chip. The CPU may generate a control mode suitable for a walking environment, and may generate a control signal for controlling an operation of a mechanical part based on the selected control mode.

The PCB refers to a board on which a desired (or alternatively, a predetermined) circuit is printed and may include the CPU and/or various storage devices. The PCB may be fixed in the housing 11.

Various types of storage devices may be included in the housing 11. The storage devices may include a magnetic disk storage device to store data by magnetizing the surface of a magnetic disk and a semiconductor memory device to store data using various types of memory semiconductors.

The power source embedded in the housing 11 may supply power to various types of parts embedded in the housing 11 or the mechanical part, for example, the first structural parts 20R and 20L, the second structural parts 30R and 30L, and the third structural parts 40R and 40L.

The body 10 may further include a waist support 12 configured to support a waist of the user. The waist support 12 may be in a shape of a curved flat plate to support the waist of the user.

The body 10 may further include a fastener 11 a configured to fasten the housing 11 to a hip portion of the user and a fastener 12a configured to fasten the waist support 12 to the waist of the user. The fastener 11a, 12a may be configured as one of a band, a belt, and a strap having elasticity.

The body 10 may include the IMU 2030. For example, the IMU 2030 may be provided outside or inside the housing 11. The IMU 2030 may be installed on the PCB embedded in the housing 11. The IMU 2030 may measure an acceleration and an angular velocity.

As illustrated in FIGS. 22 through 24, the mechanical part may include the first structural part 20R, 20L, the second structural part 30R, 30L, and the third structural part 40R, 40L.

The first structural part 20R, 20L may assist a motion of a femoral region and a hip joint of the user during a gait operation. The first structural parts 20R and 20L may include first driving devices 21R and 21L, first supports 22R and 22L, and first fasteners 23R and 23L, respectively.

The driving device 2010 may include the first driving device 21R, 21L. The description related to the driving device 2010 made with reference to FIGS. 22 and 23 may be applied to the first driving device 21R, 21L.

The first driving device 21R, 21L may be provided at a location of a corresponding hip joint of the first structural part 20R, 20L, and may generate a rotational force in a desired (or alternatively, a predetermined) direction at various magnitudes. The rotational force generated by the first driving device 21R, 21L may be applied to the first support 22R, 22L. The first driving device 21R, 21L may be set to rotate within the movement range of a hip joint of the human body.

The first driving device 21R, 21L may be driven in response to a control signal provided from the body 10. Although the first driving device 21R, 21L may be configured as one of a motor, a vacuum pump, and a hydraulic pump, it is provided as an example only.

A joint angle sensor may be installed around the first driving device 21R, 21L. The joint angle sensor may detect an angle at which the first driving device 21R, 21L rotates based on a rotational axis. The sensor 2020 may include the joint angle sensor.

The first support 22R, 22L may be physically connected to the first driving device 21R, 21L. The first support 22R, 22L may rotate in a desired (or alternatively, a predetermined) direction based on the rotational force generated by the first driving device 21R, 21L.

The first support 22R, 22L may be provided in various shapes. For example, the first support 22R, 22L may be in a shape in which a plurality of knuckles is inter-connected. Here, a joint may be provided between the knuckles. The first support 22R, 22L may bend within a desired (or alternatively, a predetermined) range by the joint. As another example, the first support 22R, 22L may be provided in a bar shape. Here, the first support 22R, 22L may be configured using a flexible material to be bendable within a desired (or alternatively, a predetermined) range.

The first fastener 23R, 23L may be provided to the first support 22R, 22L. The first fastener 23R, 23L serves to fasten the first support 22R, 22L to a corresponding femoral region of the user.

FIGS. 22 through 24 illustrate an example in which the first supports 22R and 22L are fastened to the outside of the femoral regions of the user by the first fasteners 23R and 23L, respectively. When the first support 22R, 22L rotates in response to the first driving device 21R, 21L being driven, the femoral region to which the first support 22R, 22L is fastened may rotate in the same direction in which the first support 22R, 22L rotates.

The first fastener 23R, 23L may be configured as one of a band, a belt, and a strap having elasticity, or may be configured using a metal material. FIG. 24 illustrates an example in which the first fastener 23R, 23L is configured using a chain.

The second structural part 30R, 30L may assist a motion of a lower leg and a knee joint of the user during a gait operation. The second structural parts 30R and 30L include second driving devices 31R and 31L, second supports 32R and 32L, and second fasteners 33R and 33L, respectively.

The second driving device 31R, 31L may be provided at a location of a corresponding knee joint of the second structural part 30R, 30L, and may generate a rotational force in a desired (or alternatively, a predetermined) direction at various magnitudes. The rotational force generated by the second driving device 31R, 31L may be applied to the second support 22R, 22L. The second driving device 31R, 31L may be set to rotate within a movement range of a knee joint of the human body.

The driving device 2010 may include the second driving device 31R, 31L. The description related to the hip joint made with reference to FIGS. 20 and 21 may be similarly applied to the knee joint.

The second driving device 31R, 31L may be driven in response to a control signal provided from the body 10. Although the second driving device 31R, 31L may be configured as one of a motor, a vacuum pump and a hydraulic pump, it is provided as an example only.

A joint angle sensor may be installed around the second driving device 31R, 31L. The joint angle sensor may detect an angle at which the second driving device 31R, 31L rotates based on a rotational axis. The sensor 2020 may include the joint angle sensor.

The second support 32R, 32L may be physically connected to the second driving device 31R, 31L. The second support 32R, 32L may rotate in a desired (or alternatively, a predetermined) direction based on the rotational force generated by the second driving device 31R, 31L.

The second fastener 33R, 33L may be provided to the second support 32R, 32L. The second fastener 33R, 33L serves to fasten the second support 32R, 32L to a lower leg portion of the user. FIGS. 22 through 24 illustrate an example in which the second supports 32R and 32L are fastened at the outside of lower leg portions of the user by the second fasteners 33R and 33L, respectively. If the second support 33R, 33L rotates in response to driving of the second driving device 31R, 31L, the lower leg portion to which the second support 33R, 33L is fastened may rotate in the same direction in which the second support 33R, 33L rotates.

The second fastener 33R, 33L may be configured as one of a band, a belt, and a strap having elasticity, or may be configured using a metal material.

The third structural part 40R, 40L may assist a motion of an ankle joint and related muscles of the user during a gait operation. The third structural parts 40R and 40L may include third driving devices 41R and 41L, foot supports 42R and 42L, and third fasteners 43R and 43L, respectively.

The driving device 2010 may include the third driving device 41R, 41L. The description related to the hip joint made with reference to FIGS. 20 and 21 may be similarly applied to the ankle joint.

The third driving device 41R, 41L may be provided to a corresponding ankle joint of the third structural part 40R, 40L, and may be driven in response to a control signal provided from the body 10. Similar to the first driving device 21R, 21L or the second driving device 31R, 31L, the third driving device 41R, 41L may be configured as a motor.

The foot support 42R, 42L may be provided at a location corresponding to a sole of the user, and may be physically connected to the third driving device 41R and 41L.

A pressure sensor configured to detect a weight of the user may be provided to the foot support 42R, 42L. A detection result of the pressure sensor may be used to determine whether the user is wearing the body-type walking assistance device 1, whether the user stands, whether a foot of the user is in contact with the ground, and the like. Additionally, the detection result of the pressure sensor may also be used to determine a gait state of a first leg.

The pressure sensor provided in the foot support 42R, 42L may correspond to the first pressure sensor 560 and the second pressure sensor 570.

The third fastener 43R, 43L may be provided to the foot support 42R, 42L. The third fastener 43R, 43L serves to fasten a foot of the user to the foot support 42R, 42L.

According to an aspect, the third mechanical part 40R, 40L may be the walking assistance device 500 of FIG. 5 or the walking assistance device 600 of FIG. 6. For example, the driving device 640 may be the third driving device 41R, 41L.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of controlling a driving device of a walking assistance device, the method comprising:
   capturing, via a camera attached to a first leg of a user, a leg image of a second leg of the user;
   adjusting an orientation of the leg image to generate an adjusted leg image based on at least one of acceleration information and orientation information acquired from an inertial measurement unit (IMU) attached to at least one of the first leg and the second leg;
   determining a gait state of the second leg based on the adjusted leg image;
   determining an assist torque value output to the first leg based on the gait state of the second leg; and
   controlling the driving device to output the assist torque value to the first leg.

2. The method of claim 1, wherein the camera is a multi-view camera, and the capturing of the leg image comprises:
   capturing, via the multi-view camera, a plurality of leg images; and
   generating the leg image by merging the plurality of leg images.

3. The method of claim 1, wherein the camera is an infrared camera or a thermal imaging camera.

4. The method of claim 1, wherein the determining of the gait state of the second leg comprises:
   detecting, in the leg image, a ground and the second leg; and
   determining the gait state of the second leg based on the ground and the second leg in the leg image.

5. The method of claim 4, wherein the determining of the gait state of the second leg based on the ground and the second leg in the leg image comprises:
   determining the gait state of the second leg based on an angle between the ground and the second leg in the leg image.

6. The method of claim 4, wherein the determining of the gait state of the second leg based on the ground and the second leg in the leg image comprises:
   determining a position of the second leg in the leg image; and
   determining the gait state based on the position of the second leg in the leg image.

7. The method of claim 6, wherein the determining of the gait state based on the position of the second leg in the leg image comprises:
   determining a relative position of the second leg with respect to at least two feature positions;
   determining a degree of process of a gait cycle based on the relative position; and
   determining the gait state based on the degree of process of the gait cycle.

8. The method of claim 6, wherein the determining of the gait state based on the position of the second leg in the leg image comprises:
   determining whether the second leg has passed a threshold position in a set direction based on the position of the second leg in the leg image; and
   determining the gait state to be a target gait state in response to the second leg passing the threshold position in the set direction.

9. The method of claim 8, wherein the determining of the assist torque value output to the first leg comprises:
   determining the assist torque value for push-off of the first leg in response to the gait state of the second leg being the target gait state.

10. The method of claim 8, wherein the determining of the assist torque value output to the first leg comprises:
    determining the assist torque value for dorsiflexion of the first leg in response to the gait state of the second leg being the target gait state.

11. The method of claim 1, wherein the determining of the assist torque value output to the first leg comprises:
    determining the assist torque value from an assist torque table or an assist torque trajectory mapped to the gait state of the second leg.

12. The method of claim 1, wherein the determining of the assist torque value output to the first leg comprises:
    determining a gait state of the first leg based on the gait state of the second leg; and
    determining the assist torque value output to the first leg based on the gait state of the first leg.

13. The method of claim 12, wherein the determining of the gait state of the first leg comprises:

acquiring a pressure value from at least one pressure sensor attached to the first leg; and determining the gait state of the first leg based on the pressure value and the gait state of the second leg.

14. A non-transitory computer-readable medium comprising computer readable instructions that, when executed, configure a computer to perform the method of claim 1.

15. A walking assistance device for providing an assist torque to an ankle of a first leg of a user, the walking assistance device comprising:

a memory including a program for providing the assist torque; and a processor configured to execute the program to, capture, via a camera attached to the first leg of the user, a leg image of a second leg of the user, adjust an orientation of the leg image to generate an adjusted leg image based on at least one of acceleration information and orientation information acquired from an inertial measurement unit (IMU) attached to at least one of the first leg and the second leg, determine a gait state of the second leg based on the adjusted leg image, determine an assist torque value output to the first leg based on the gait state of the second leg, and control a driving device to output the assist torque value to the first leg such that the driving device provides the assist torque to the ankle of the first leg of the user.

16. A walking assistance device for assisting walking of a user, the walking assistance device comprising:

a camera configured to attach to a first leg of the user such that the camera is configured to capture a leg image of a second leg of the user;

a processor configured to, adjust an orientation of the leg image to generate an adjusted leg image based on at least one of acceleration information and orientation information acquired from an inertial measurement unit (IMU) attached to at least one of the first leg and the second leg, determine a gait state of the second leg based on the adjusted leg image, and determine an assist torque value to output to the first leg based on the gait state of the second leg; and a driving device configured to generate an assist torque having the assist torque value.

* * * * *